United States Patent
Teunissen et al.

(10) Patent No.: US 10,093,914 B2
(45) Date of Patent: Oct. 9, 2018

(54) XYLOSE ISOMERASE GENES AND THEIR USE IN FERMENTATION OF PENTOSE SUGARS

(71) Applicant: DSM IP ASSETS B.V., Heerlen (NL)

(72) Inventors: Aloysius Wilhelmus Rudolphus Hubertus Teunissen, Rotterdam (NL); Johannes Adrianus Maria De Bont, Wageningen (NL)

(73) Assignee: DSM IP ASSETS B.V., Heerlen (NL)

( * ) Notice: Subject to any disclaimer, the term of this patent is extended or adjusted under 35 U.S.C. 154(b) by 60 days.

(21) Appl. No.: 15/093,726

(22) Filed: Apr. 7, 2016

(65) Prior Publication Data

US 2016/0230162 A1   Aug. 11, 2016

Related U.S. Application Data

(62) Division of application No. 13/142,124, filed as application No. PCT/NL2009/050803 on Dec. 24, 2009, now Pat. No. 9,334,488.

(60) Provisional application No. 61/140,795, filed on Dec. 24, 2008.

(30) Foreign Application Priority Data

Dec. 24, 2008  (EP) .................................... 08172919

(51) Int. Cl.
| | |
|---|---|
| C12N 1/19 | (2006.01) |
| C12P 5/02 | (2006.01) |
| C12P 17/10 | (2006.01) |
| C12P 7/14 | (2006.01) |
| C12P 13/04 | (2006.01) |
| C12P 7/56 | (2006.01) |
| C12P 7/54 | (2006.01) |
| C12P 7/52 | (2006.01) |
| C12P 7/48 | (2006.01) |
| C12P 7/46 | (2006.01) |
| C12P 7/40 | (2006.01) |
| C12P 7/20 | (2006.01) |
| C12P 7/18 | (2006.01) |
| C12P 7/16 | (2006.01) |
| C12P 7/06 | (2006.01) |
| C12P 7/42 | (2006.01) |
| C12P 35/00 | (2006.01) |
| C12N 15/52 | (2006.01) |
| C12N 9/90 | (2006.01) |
| C12N 9/92 | (2006.01) |

(52) U.S. Cl.
CPC ................ *C12N 9/90* (2013.01); *C12N 9/92* (2013.01); *C12N 15/52* (2013.01); *C12P 5/026* (2013.01); *C12P 7/06* (2013.01); *C12P 7/14* (2013.01); *C12P 7/16* (2013.01); *C12P 7/18* (2013.01); *C12P 7/20* (2013.01); *C12P 7/40* (2013.01); *C12P 7/42* (2013.01); *C12P 7/46* (2013.01); *C12P 7/48* (2013.01); *C12P 7/52* (2013.01); *C12P 7/54* (2013.01); *C12P 7/56* (2013.01); *C12P 13/04* (2013.01); *C12P 17/10* (2013.01); *C12P 35/00* (2013.01); *C12Y 503/01005* (2013.01); *Y02E 50/10* (2013.01); *Y02E 50/16* (2013.01); *Y02E 50/17* (2013.01); *Y02P 20/52* (2015.11)

(58) Field of Classification Search
CPC .... C12N 9/92; C12P 17/10; C12P 7/06; C12P 7/16; C12P 7/18; C12P 7/20; C12P 7/40; C12P 7/42; C12P 7/46; C12P 7/48; C12P 7/52; C12P 7/54; C12P 7/56; C12P 13/04; C12P 35/00; C12Y 503/01005; Y02E 50/16
See application file for complete search history.

(56) References Cited

U.S. PATENT DOCUMENTS 7,317,146 B2   1/2008   Singletary et al.

FOREIGN PATENT DOCUMENTS

| WO | 03/062430 A1 | 7/2003 |
|---|---|---|
| WO | 03062340 A1 | 7/2003 |
| WO | 2003/095627 | 11/2003 |
| WO | 2004044129 A2 | 5/2004 |
| WO | 2004099381 A2 | 11/2004 |
| WO | 2006/009434 | 4/2006 |

OTHER PUBLICATIONS

Sadowski et al., Current Opinion in Structural Biology 19:357-362, 2009.*
Sebaihia et al., GenBank accession No. Q184Q2, Nov. 28, 2006.*
Gen Bank xylose isomerase [Ciona intestionalis] XP002125575 Oct. 2014.
Guo et al., PNAS 101(25):9205-9210, 2004.

(Continued)

*Primary Examiner* — Delia M Ramirez
(74) *Attorney, Agent, or Firm* — McBee Moore Woodward & Vanik IP, LLC; Susan McBee; Chester Moore

(57) ABSTRACT

The present invention relates to eukaryotic cells which have the ability to isomerize xylose directly into xylulose. The cells have acquired this ability by transformation with nucleotide sequences coding for a xylose isomerase that has one or more specific sequence elements typical for isomerases having the ability of functional expression in yeasts, such as e.g. xylose isomerases obtainable from a bacterium of the genera *Clostridium* and *Fusobacterium* or a tunicate form the genus *Ciona*. The cell preferably is a yeast or a filamentous fungus, more preferably a yeast is capable of anaerobic alcoholic fermentation.

23 Claims, 1 Drawing Sheet
Specification includes a Sequence Listing.

(56) References Cited

OTHER PUBLICATIONS

Branden et al., Introduction to Protein Structure, Garland Publishing Inc., New York, p. 247, 1991.
Seffernick et al., J. Bacteriol. 183(8):2405-2410, 2001.
Witkowski et al., Biochemistry 38:11643-11650, 1999.
Zhou et al., Cell Mol Life Sci 63(19-20):2260-2290, 2006.
Kozak, M., Gene 234:187-208, 1999.
Wisselink et al., Applied and Environmental Microbiology 73(15):4881-4891, Jun. 1, 2007.

* cited by examiner

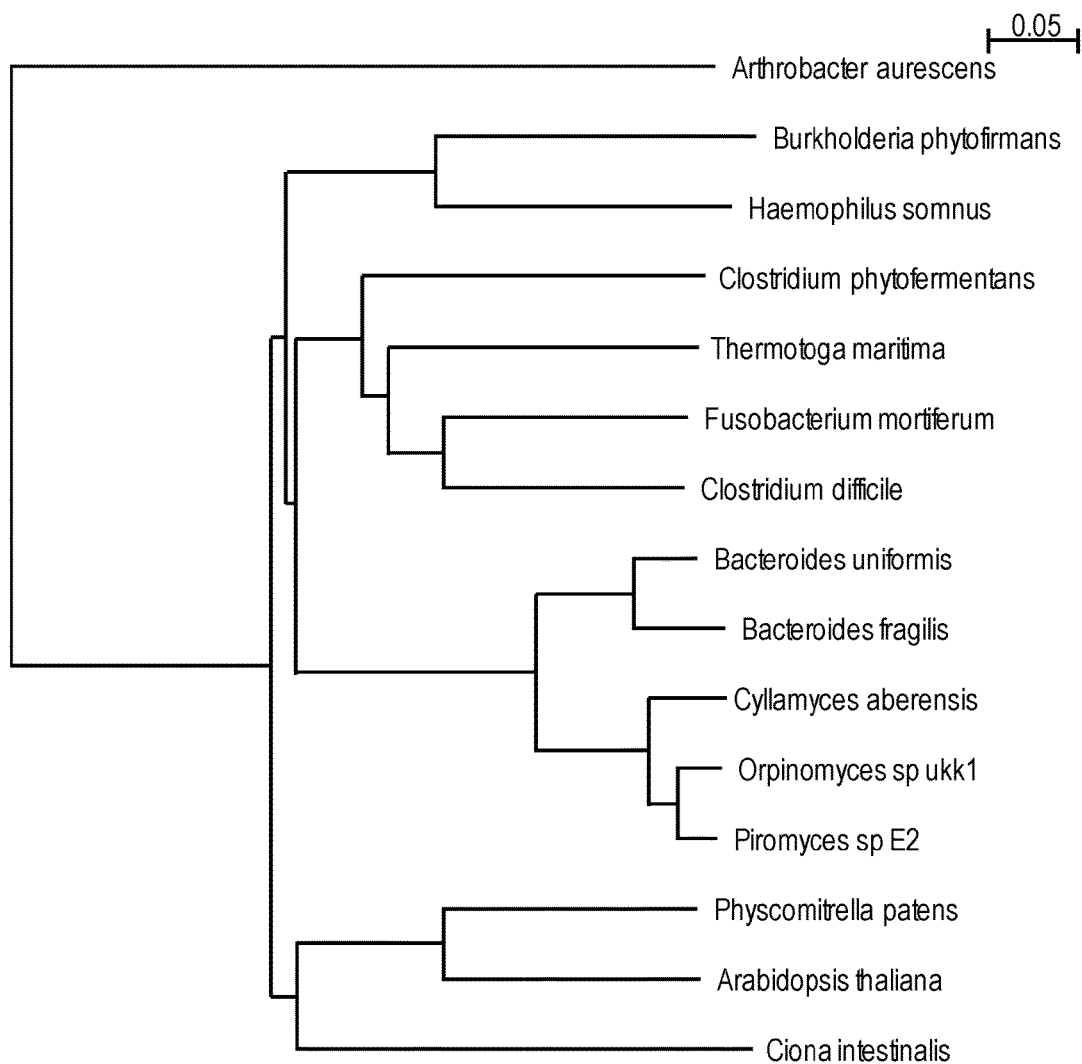

SEQUENCE LISTING

<160> NUMBER OF SEQ ID NOS: 40

<210> SEQ ID NO 1
<211> LENGTH: 445
<212> TYPE: PRT
<213> ORGANISM: Clostridium difficile

<400> SEQUENCE: 1

```
Met Asn Glu Ile Phe Lys Gly Ile Gly Gln Ile Lys Phe Glu Gly Val
1               5                   10                  15

Lys Ser Asn Asn Glu Leu Ala Phe Arg Tyr Tyr Asn Pro Glu Gln Val
            20                  25                  30

Val Gly Asn Lys Thr Met Lys Glu His Leu Arg Phe Ala Met Ser Tyr
        35                  40                  45

Trp His Thr Leu Cys Gly Glu Gly Asn Asp Pro Phe Gly Val Gly Thr
    50                  55                  60

Val Glu Arg Pro Trp Asn Asn Ile Thr Asp Pro Ile Glu Ile Ala Lys
65                  70                  75                  80

Ile Lys Val Asp Ala Gly Phe Glu Phe Met Ser Lys Met Gly Ile Glu
                85                  90                  95

Tyr Phe Cys Phe His Asp Arg Asp Ile Ala Pro Glu Gly Arg Asp Leu
            100                 105                 110

Glu Glu Thr Asn Lys Ile Leu Asp Glu Ile Val Glu Tyr Ile Lys Ala
            115                 120                 125

Asn Met Glu Lys Thr Gly Ile Lys Leu Leu Trp Gly Thr Ala Asn Met
130                 135                 140

Phe Gly Asn Pro Arg Phe Val His Gly Ala Ser Thr Thr Cys Asn Ala
145                 150                 155                 160

Asp Val Tyr Ala Tyr Ala Ala Ala Gln Val Lys Lys Ala Met Glu Ile
                165                 170                 175

Thr Lys Tyr Leu Gly Gly Glu Asn Phe Val Phe Trp Gly Gly Arg Glu
            180                 185                 190

Gly Tyr Glu Thr Leu Leu Asn Thr Asn Thr Glu Leu Glu Met Asp Asn
            195                 200                 205

Phe Ala Arg Phe Leu Gln Met Ala Val Asp Tyr Ala Lys Glu Ile Gly
210                 215                 220

Phe Thr Gly Gln Phe Leu Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255

Tyr Asn Leu Asp Lys Tyr Phe Lys Val Asn Ile Glu Ala Asn His Ala
            260                 265                 270

Thr Leu Ala Gly His Thr Phe Gln His Glu Leu Asn Ile Ala Arg Ile
            275                 280                 285

Asn Asn Val Leu Gly Ser Ile Asp Ala Asn Gln Gly Asp Leu Leu Leu
290                 295                 300

Gly Trp Asp Thr Asp Gln Phe Pro Thr Asn Ile Tyr Asp Ala Thr Leu
305                 310                 315                 320

Ala Met Tyr Glu Val Leu Lys Gln Gly Gly Ile Ala Pro Gly Gly Phe
                325                 330                 335

Asn Phe Asp Ser Lys Val Arg Arg Ala Ser Phe Glu Val Glu Asp Leu
            340                 345                 350

Phe Leu Ala Tyr Ile Ala Gly Met Asp Thr Phe Ala Lys Gly Leu Leu
            355                 360                 365

Ile Ala His Lys Leu Leu Glu Asp Glu Val Phe Glu Asn Phe Thr Lys
370                 375                 380

Glu Arg Tyr Ala Ser Phe Ser Glu Gly Ile Gly Lys Asp Ile Val Glu
385                 390                 395                 400

Gly Lys Val Gly Phe Lys Glu Leu Glu Ser Tyr Ala Leu Gln Met Pro
```

405                 410                 415
Val Ile Lys Asn Lys Ser Gly Arg Gln Glu Met Leu Glu Ala Ile Leu
                420                 425                 430

Asn Arg Tyr Ile Tyr Glu Val Asp Thr Ile Ser Asn Lys
            435                 440                 445

<210> SEQ ID NO 2
<211> LENGTH: 456
<212> TYPE: PRT
<213> ORGANISM: Ciona intestinalis

<400> SEQUENCE: 2

Met Ser Ser Phe Ala Pro Ala Ser Gly Lys Ser Asp Leu Ala Glu Ala
1               5                   10                  15

Gly Ser Leu Leu Thr Lys Tyr Pro Leu Glu Val Lys Lys Ile Pro Tyr
                20                  25                  30

Lys Pro Asp Ala Lys Val Asp Asp Val Leu Cys Phe Arg His Tyr Asn
                35                  40                  45

Glu Ser Glu Val Val Met Gly Lys Pro Met Ser Asp Trp Leu Arg Phe
    50                  55                  60

Ser Val Cys Tyr Trp His Thr Phe Arg Gly Thr Gly Ala Asp Pro Phe
65                  70                  75                  80

Gly Phe Pro Thr Leu Val Arg Pro Trp Asp Asp Gly Thr Asp Ser Ile
                85                  90                  95

Glu Asn Ala Glu Arg Arg Met Arg Val Ala Phe Asp Phe Met Ser Lys
                100                 105                 110

Leu Gly Val Lys Tyr Trp Thr Phe His Asp Arg Asp Ile Ala Pro Glu
                115                 120                 125

Gly Val Thr Leu Ser Glu Thr Asn Ala Asn Leu Asp Arg Leu Ala Glu
                130                 135                 140

Leu Ala Ser Gln Leu Gln Gly Glu Thr Gly Ile Lys Leu Leu Trp Asn
145                 150                 155                 160

Thr Cys Asn Leu Phe Ala His Pro Arg Tyr Ser Asn Gly Ala Ala Thr
                165                 170                 175

Asn Ala Asp Ala His Val Val Ala Tyr Ala Ala Ala Gln Val Lys Lys
                180                 185                 190

Ser Leu Glu Ile Gly Lys Lys Leu Gly Ala Glu Asn Phe Val Phe Trp
                195                 200                 205

Gly Gly Arg Glu Gly Tyr His Thr Leu Leu Asn Thr Asn Val Arg Glu
                210                 215                 220

Glu Leu Asp Asn Leu Ala Asn Phe Phe Lys Met Val Val Ala Tyr Lys
225                 230                 235                 240

Lys Lys Ile Gly Phe Thr Gly Gln Phe Leu Ile Glu Pro Lys Pro Lys
                245                 250                 255

Glu Pro Ser Lys His Gln Tyr Asp Tyr Asp Ala Met Thr Val Ile Ala
                260                 265                 270

Phe Leu Lys Thr Tyr Asp Leu Asp Lys Asp Phe Lys Leu Asn Ile Glu
                275                 280                 285

Pro Asn His Thr Thr Leu Ala Gly His Cys His Glu His Asp Val Val
                290                 295                 300

Met Ala Ser Ala Tyr Asn Met Leu Gly Ser Val Asp Ser Asn Thr Gly
305                 310                 315                 320

Ser Pro Asp Leu Gly Trp Asp Thr Asp Gln Phe Pro Met Asp Val Lys
                325                 330                 335

-continued

```
Asn Ala Thr Met Ile Met Gln Thr Val Leu Glu Gln Gly Gly Leu Ala
                340                 345                 350

Pro Gly Gly Leu Asn Phe Asp Cys Lys Val Arg Arg Glu Ser Thr Asp
            355                 360                 365

Val Ile Asp Met Met Ile Ala His Val Gly Ala Met Asp Cys Phe Ala
        370                 375                 380

Lys Ala Leu Lys Ile Ala Ala Lys Ile Arg Glu Asp Gly Val Leu Gly
385                 390                 395                 400

Lys Met Lys Lys Glu Arg Tyr Ala Ser Phe Gly Ser Gly Leu Gly Leu
                405                 410                 415

Lys Ile Lys Thr Gly Thr Ala Thr Leu Glu Glu Cys Asp Ser Phe Ile
            420                 425                 430

Gln Glu Asn Gly Glu Pro Ala Lys Leu Ser Gly Lys Gln Glu Met Phe
        435                 440                 445

Glu Ala Val Leu Asn Arg Tyr Phe
    450                 455

<210> SEQ ID NO 3
<211> LENGTH: 437
<212> TYPE: PRT
<213> ORGANISM: Piromyces sp.
<220> FEATURE:
<221> NAME/KEY: misc_feature
<223> OTHER INFORMATION: xylose isomerase

<400> SEQUENCE: 3

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
                20                  25                  30

Glu Val Met Gly Lys Lys Met Lys Asp Trp Leu Arg Phe Ala Met Ala
            35                  40                  45

Trp Trp His Thr Leu Cys Ala Glu Gly Ala Asp Gln Phe Gly Gly Gly
        50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240
```

```
Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
                340                 345                 350

Ile Ile Ile Ala His Val Ser Gly Met Asp Ala Met Ala Arg Ala Leu
                355                 360                 365

Glu Asn Ala Ala Lys Leu Leu Gln Glu Ser Pro Tyr Thr Lys Met Lys
        370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
                420                 425                 430

Val Ala Met Tyr Gln
            435

<210> SEQ ID NO 4
<211> LENGTH: 437
<212> TYPE: PRT
<213> ORGANISM: Cyllamyces aberensis

<400> SEQUENCE: 4

Met Val Lys Glu Tyr Phe Pro Ala Ile Gln Lys Ile Lys Phe Glu Gly
1               5                   10                  15

Lys Asp Ser Lys Asn Pro Met Ala Phe His Tyr Tyr Asp Ala Glu Lys
                20                  25                  30

Glu Ile Met Gly Lys Lys Met Lys Asp Trp Leu Arg Phe Ala Met Ala
            35                  40                  45

Trp Trp His Thr Leu Cys Ala Glu Gly Ser Asp Gln Phe Gly Pro Gly
    50                  55                  60

Thr Lys Thr Phe Pro Trp Asn Glu Gly Thr Asp Pro Ile Glu Lys Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Asp Glu Gly Lys Asn
                100                 105                 110

Val Glu Glu Tyr Glu Lys Asn Leu Lys Thr Ile Val Ala Tyr Leu Lys
            115                 120                 125

Glu Lys Gln Lys Glu Thr Gly Ile Lys Leu Leu Trp Ser Thr Ala Asn
        130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
```

```
                      165                 170                 175
Ala Gly Ile Glu Leu Gly Ala Glu Asn Tyr Val Phe Trp Gly Gly Arg
                180                 185                 190

Glu Gly Tyr Met Ser Leu Leu Asn Thr Asp Gln Lys Arg Glu Lys Glu
            195                 200                 205

His Met Ala Met Met Leu Gly Leu Ala Arg Asp Tyr Ala Arg Ser Lys
        210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala His Gly Leu Asp Lys Asp Phe Lys Ile Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Thr Thr Gly Gly
                325                 330                 335

Thr Asn Phe Asp Ala Lys Thr Arg Arg Asn Ser Thr Asp Leu Glu Asp
                340                 345                 350

Ile Ile Ile Ala His Ile Ser Gly Met Asp Ala Met Ala Arg Ala Leu
            355                 360                 365

Glu Asn Ala Ala Lys Leu Leu Thr Glu Ser Pro Tyr Lys Lys Met Lys
        370                 375                 380

Ala Asp Arg Tyr Ala Ser Phe Asp Ser Gly Met Gly Lys Asp Phe Glu
385                 390                 395                 400

Asp Gly Lys Leu Thr Phe Glu Gln Val Tyr Glu Tyr Gly Lys Lys Val
                405                 410                 415

Asn Glu Pro Lys Gln Thr Ser Gly Lys Gln Glu Leu Tyr Glu Ala Ile
            420                 425                 430

Val Ala Met Tyr Met
        435

<210> SEQ ID NO 5
<211> LENGTH: 437
<212> TYPE: PRT
<213> ORGANISM: Orpinomyces sp.

<400> SEQUENCE: 5

Met Thr Lys Glu Tyr Phe Pro Thr Ile Gly Lys Ile Arg Phe Glu Gly
1               5                   10                  15

Lys Asp Ser Lys Asn Pro Met Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Asp Gly Ala Asp Gln Phe Gly Val Gly
    50                  55                  60

Thr Lys Ser Phe Pro Trp Asn Glu Gly Thr Asp Pro Ile Ala Ile Ala
65                  70                  75                  80

Lys Gln Lys Val Asp Ala Gly Phe Glu Ile Met Thr Lys Leu Gly Ile
                85                  90                  95
```

```
Glu His Tyr Cys Phe His Asp Val Asp Leu Val Ser Glu Gly Asn Ser
            100                 105                 110

Ile Glu Glu Tyr Glu Ser Asn Leu Lys Gln Val Ala Tyr Leu Lys
        115                 120                 125

Gln Lys Gln Gln Glu Thr Gly Ile Lys Leu Leu Trp Ser Thr Ala Asn
    130                 135                 140

Val Phe Gly Asn Pro Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Ile Ser Gly Met Asp Ala Met Ala Arg Ala Leu
        355                 360                 365

Glu Asn Ala Ala Lys Leu Leu Gln Glu Ser Pro Tyr Cys Asn Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Val Thr Ser Gly Lys Gln Glu Leu Tyr Glu Ala Ile
            420                 425                 430

Val Ala Met Tyr Gln
        435

<210> SEQ ID NO 6
<211> LENGTH: 438
<212> TYPE: PRT
<213> ORGANISM: Bacteroides thetaiotaomicron
<220> FEATURE:
<221> NAME/KEY: misc_feature
<223> OTHER INFORMATION: xylose isomerase

<400> SEQUENCE: 6

Met Ala Thr Lys Glu Phe Phe Pro Gly Ile Glu Lys Ile Lys Phe Glu
1               5                   10                  15
```

```
Gly Lys Asp Ser Lys Asn Pro Met Ala Phe Arg Tyr Tyr Asp Ala Glu
             20                  25                  30
Lys Val Ile Asn Gly Lys Lys Met Lys Asp Trp Leu Arg Phe Ala Met
         35                  40                  45
Ala Trp Trp His Thr Leu Cys Ala Glu Gly Asp Gln Phe Gly Gly
 50                  55                  60
Gly Thr Lys Gln Phe Pro Trp Asn Gly Asn Ala Asp Ala Ile Gln Ala
65                  70                  75                  80
Ala Lys Asp Lys Met Asp Ala Gly Phe Glu Phe Met Gln Lys Met Gly
                 85                  90                  95
Ile Glu Tyr Tyr Cys Phe His Asp Val Asp Leu Val Ser Glu Gly Ala
             100                 105                 110
Ser Val Glu Glu Tyr Glu Ala Asn Leu Lys Glu Ile Val Ala Tyr Ala
         115                 120                 125
Lys Gln Lys Gln Ala Glu Thr Gly Ile Lys Leu Leu Trp Gly Thr Ala
130                 135                 140
Asn Val Phe Gly His Ala Arg Tyr Met Asn Gly Ala Ala Thr Asn Pro
145                 150                 155                 160
Asp Phe Asp Val Val Ala Arg Ala Ala Val Gln Ile Lys Asn Ala Ile
                 165                 170                 175
Asp Ala Thr Ile Glu Leu Gly Gly Glu Asn Tyr Val Phe Trp Gly Gly
             180                 185                 190
Arg Glu Gly Tyr Met Ser Leu Leu Asn Thr Asp Gln Lys Arg Glu Lys
         195                 200                 205
Glu His Leu Ala Gln Met Leu Thr Ile Ala Arg Asp Tyr Ala Arg Ala
     210                 215                 220
Arg Gly Phe Lys Gly Thr Phe Leu Ile Glu Pro Lys Pro Met Glu Pro
225                 230                 235                 240
Thr Lys His Gln Tyr Asp Val Asp Thr Glu Thr Val Ile Gly Phe Leu
                 245                 250                 255
Lys Ala His Gly Leu Asp Lys Asp Phe Lys Val Asn Ile Glu Val Asn
             260                 265                 270
His Ala Thr Leu Ala Gly His Thr Phe Glu His Glu Leu Ala Val Ala
         275                 280                 285
Val Asp Asn Gly Met Leu Gly Ser Ile Asp Ala Asn Arg Gly Asp Tyr
     290                 295                 300
Gln Asn Gly Trp Asp Thr Asp Gln Phe Pro Ile Asp Asn Tyr Glu Leu
305                 310                 315                 320
Thr Gln Ala Met Met Gln Ile Ile Arg Asn Gly Gly Leu Gly Thr Gly
                 325                 330                 335
Gly Thr Asn Phe Asp Ala Lys Thr Arg Arg Asn Ser Thr Asp Leu Glu
             340                 345                 350
Asp Ile Phe Ile Ala His Ile Ala Gly Met Asp Ala Met Ala Arg Ala
         355                 360                 365
Leu Glu Ser Ala Ala Ala Leu Leu Asp Glu Ser Pro Tyr Lys Lys Met
     370                 375                 380
Leu Ala Asp Arg Tyr Ala Ser Phe Asp Gly Gly Lys Gly Lys Glu Phe
385                 390                 395                 400
Glu Asp Gly Lys Leu Thr Leu Glu Asp Val Val Ala Tyr Ala Lys Thr
                 405                 410                 415
Lys Gly Glu Pro Lys Gln Thr Ser Gly Lys Gln Glu Leu Tyr Glu Ala
             420                 425                 430
```

```
Ile Leu Asn Met Tyr Cys
        435
```

<210> SEQ ID NO 7
<211> LENGTH: 439
<212> TYPE: PRT
<213> ORGANISM: Bacteroides fragilis

<400> SEQUENCE: 7

```
Met Ala Thr Lys Glu Tyr Phe Pro Gly Ile Gly Lys Ile Lys Phe Glu
1               5                   10                  15

Gly Lys Asp Ser Lys Asn Pro Met Ala Phe Arg Tyr Tyr Asp Ala Glu
            20                  25                  30

Lys Met Ile Asn Gly Arg Ser Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asp Pro Asp Pro Val Gln Ala
65                  70                  75                  80

Ala Lys Asn Lys Met Asp Ala Gly Phe Glu Phe Met Gln Lys Met Gly
                85                  90                  95

Ile Gly Tyr Tyr Cys Phe His Asp Val Asp Leu Val Thr Glu Ala Asp
            100                 105                 110

Ser Ile Glu Ala Tyr Glu Ala Asn Leu Lys Glu Leu Val Ala Tyr Ala
        115                 120                 125

Lys Gln Lys Gln Ala Glu Thr Gly Ile Lys Leu Leu Trp Gly Thr Ala
    130                 135                 140

Asn Val Phe Ser His Ala Arg Tyr Met Asn Gly Ala Ala Thr Asn Pro
145                 150                 155                 160

Asp Phe Asp Val Val Ala Arg Ala Val Gln Ile Lys Asn Ala Ile
                165                 170                 175

Asp Ala Thr Ile Glu Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Gly Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asn Gln Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Asp Gly Leu Gly Asn Gly
                325                 330                 335

Gly Thr Asn Phe Asp Ala Lys Thr Arg Arg Asn Ser Thr Asp Pro Glu
            340                 345                 350

Asp Ile Phe Ile Ala His Ile Ala Gly Met Asp Ala Met Ala Arg Ala
        355                 360                 365
```

Leu Glu Ser Ala Ala Asn Leu Leu Asn Glu Ser Pro Tyr Gln Lys Met
            370                 375                 380

Leu Ser Asp Arg Tyr Ala Ser Phe Asp Ala Gly Lys Gly Lys Glu Phe
385                 390                 395                 400

Glu Glu Gly Lys Leu Ser Leu Glu Glu Leu Val Ala Tyr Ala Lys Ala
                405                 410                 415

Asn Gly Glu Pro Lys Gln Thr Ser Gly Gln Gln Glu Leu Tyr Glu Ala
            420                 425                 430

Leu Val Asn Ile Tyr Ser Leu
            435

<210> SEQ ID NO 8
<211> LENGTH: 440
<212> TYPE: PRT
<213> ORGANISM: Burkholderia phytofirmans

<400> SEQUENCE: 8

Met Ser Tyr Phe Glu His Ile Pro Glu Ile Arg Tyr Glu Gly Pro Gln
1               5                   10                  15

Ser Asp Asn Pro Leu Ala Tyr Arg His Tyr Asp Lys Ser Lys Lys Val
            20                  25                  30

Leu Gly Lys Thr Leu Glu Glu His Leu Arg Ile Ala Val Cys Tyr Trp
        35                  40                  45

His Thr Phe Val Trp Pro Gly Val Asp Ile Phe Gly Gln Gly Thr Phe
    50                  55                  60

Arg Arg Pro Trp Gln Gln Ala Gly Asp Ala Met Glu Arg Ala Gln Gln
65                  70                  75                  80

Lys Ala Asp Ser Ala Phe Glu Phe Phe Ser Lys Leu Gly Thr Pro Tyr
                85                  90                  95

Tyr Thr Phe His Asp Thr Asp Val Ser Pro Glu Gly Ser Asn Leu Lys
            100                 105                 110

Glu Tyr Ser Glu Asn Phe Leu Arg Ile Thr Asp Tyr Leu Ala Arg Lys
        115                 120                 125

Gln Glu Ser Thr Gly Ile Lys Leu Leu Trp Gly Thr Ala Asn Leu Phe
130                 135                 140

Ser His Pro Arg Tyr Ala Ala Gly Ala Ala Thr Ser Pro Asp Pro Glu
145                 150                 155                 160

Val Phe Ala Phe Ala Ala Thr Gln Val Arg His Ala Leu Asp Ala Thr
                165                 170                 175

Gln Arg Leu Gly Gly Asp Asn Tyr Val Leu Trp Gly Gly Arg Glu Gly
            180                 185                 190

Tyr Asp Thr Leu Leu Asn Thr Asp Leu Val Arg Glu Arg Asp Gln Leu
        195                 200                 205

Ala Arg Phe Leu His Met Val Val Asp His Ala His Lys Ile Gly Phe
210                 215                 220

Lys Gly Ser Leu Leu Ile Glu Pro Lys Pro Gln Glu Pro Thr Lys His
225                 230                 235                 240

Gln Tyr Asp Tyr Asp Val Ala Thr Val His Gly Phe Leu Leu Gln His
                245                 250                 255

Gly Leu Asp Lys Glu Ile Arg Val Asn Ile Glu Ala Asn His Ala Thr
            260                 265                 270

Leu Ala Gly His Ser Phe His His Glu Ile Ala Thr Ala Tyr Ala Leu
        275                 280                 285

Gly Ile Phe Gly Ser Val Asp Ala Asn Arg Gly Asp Pro Gln Asn Gly

```
            290                 295                 300

Trp Asp Thr Asp Gln Phe Pro Asn Ser Val Glu Glu Leu Thr Leu Ala
305                 310                 315                 320

Phe Tyr Glu Ile Leu Lys His Gly Gly Phe Thr Thr Gly Gly Met Asn
            325                 330                 335

Phe Asp Ser Lys Val Arg Arg Gln Ser Val Asp Pro Glu Asp Leu Phe
            340                 345                 350

Tyr Gly His Ile Gly Ala Ile Asp Asn Leu Ala Leu Ala Val Glu Arg
            355                 360                 365

Ala Ala Val Leu Ile Glu Asn Asp Arg Leu Asp Gln Phe Lys Arg Gln
            370                 375                 380

Arg Tyr Ser Gly Trp Asp Ala Glu Phe Gly Arg Lys Ile Ser Ser Gly
385                 390                 395                 400

Asp Tyr Ser Leu Ser Ala Leu Ala Glu Glu Ala Met Ala Arg Gly Leu
            405                 410                 415

Asn Pro Gln His Ala Ser Gly His Gln Glu Leu Met Glu Asn Ile Val
            420                 425                 430

Asn Gln Ala Ile Tyr Ser Gly Arg
            435                 440

<210> SEQ ID NO 9
<211> LENGTH: 395
<212> TYPE: PRT
<213> ORGANISM: Arthrobacter aurescens

<400> SEQUENCE: 9

Met Thr Pro Gln Pro Thr Pro Gln Asp Arg Phe Thr Phe Gly Leu Trp
1               5                   10                  15

Thr Val Gly Trp Thr Gly Ala Asp Pro Phe Gly Val Ala Thr Arg Pro
            20                  25                  30

Ala Leu Asp Pro Val Glu Ala Val His Lys Leu Ser Glu Leu Gly Ala
            35                  40                  45

Tyr Gly Ile Thr Phe His Asp Asn Asp Leu Val Pro Phe Asp Ala Thr
    50                  55                  60

Ala Ser Glu Arg Asp Leu Ile Leu Lys Asn Phe Lys Ala Ala Leu Ala
65                  70                  75                  80

Glu Thr Gly Leu Lys Thr Pro Met Val Thr Thr Asn Leu Phe Ser His
            85                  90                  95

Pro Val Phe Lys Asp Gly Gly Phe Thr Ser Asn Asp Arg Ser Ile Arg
            100                 105                 110

Arg Phe Ala Leu Ser Lys Ile Leu Arg Asn Ile Asp Leu Ala Ala Glu
            115                 120                 125

Leu Gly Ala Glu Thr Phe Val Met Trp Gly Gly Arg Glu Gly Ser Glu
            130                 135                 140

Tyr Asp Gly Ser Lys Asp Leu Ser Ala Ala Leu Asp Arg Met Lys Glu
145                 150                 155                 160

Gly Val Asp Thr Ala Ala Gly Tyr Ile Lys Glu Lys Gly Tyr Gly Leu
            165                 170                 175

Arg Ile Ala Leu Glu Pro Lys Pro Asn Glu Pro Arg Gly Asp Ile Phe
            180                 185                 190

Leu Pro Thr Val Gly His Gly Leu Ala Phe Ile Ala Gln Leu Glu His
            195                 200                 205

Gly Asp Ile Val Gly Leu Asn Pro Glu Thr Gly His Glu Gln Met Ala
            210                 215                 220
```

```
Gly Leu Asn Phe Thr His Gly Ile Ala Gln Ala Leu Trp Ala Gly Lys
225                 230                 235                 240

Leu Phe His Ile Asp Leu Asn Gly Gln Arg Gly Ile Lys Tyr Asp Gln
            245                 250                 255

Asp Leu Val Phe Gly His Gly Asp Leu Thr Ser Ala Phe Phe Thr Val
            260                 265                 270

Asp Leu Leu Glu Asn Gly Phe Pro Asn Gly Gly Pro Lys Tyr Asp Gly
        275                 280                 285

Pro Arg His Phe Asp Tyr Lys Pro Ser Arg Thr Asp Gly Tyr Asp Gly
    290                 295                 300

Val Trp Glu Ser Ala Lys Ser Asn Met Ser Met Tyr Leu Leu Leu Lys
305                 310                 315                 320

Glu Arg Ala Leu Ala Phe Arg Ala Asp Pro Glu Val Gln Glu Ala Leu
                325                 330                 335

Ala Thr Ser Gly Val Phe Glu Leu Gly Glu Pro Thr Leu Asn Ala Gly
            340                 345                 350

Glu Thr Thr Ala Asp Leu Leu Ala Asp Ala Ser Ala Phe Asp Thr Phe
        355                 360                 365

Asn Ala Asp Gln Ala Ala Glu Arg Ser Phe Ala Phe Val Arg Leu Asn
370                 375                 380

Gln Leu Ala Ile Glu His Leu Leu Gly Ala Arg
385                 390                 395

<210> SEQ ID NO 10
<211> LENGTH: 444
<212> TYPE: PRT
<213> ORGANISM: Thermotoga maritima

<400> SEQUENCE: 10

Met Ala Glu Phe Phe Pro Glu Ile Pro Lys Ile Gln Phe Glu Gly Lys
1               5                   10                  15

Glu Ser Thr Asn Pro Leu Ala Phe Arg Phe Tyr Asp Pro Asn Glu Val
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Glu Arg Pro Trp Asn Arg Phe Ser Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Leu Glu Leu Glu Asn
        195                 200                 205
```

```
Leu Ala Arg Phe Leu Arg Met Ala Val Glu Tyr Ala Lys Lys Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Asn
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
    290                 295                 300

Gly Trp Asp Thr Asp Gln Phe Pro Thr Asn Ile Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Ile Ala Tyr Lys Leu Ala Lys Asp Gly Val Phe Asp Lys Phe Ile Glu
    370                 375                 380

Glu Lys Tyr Arg Ser Phe Lys Glu Gly Ile Gly Lys Glu Ile Val Glu
385                 390                 395                 400

Gly Lys Thr Asp Phe Glu Lys Leu Glu Glu Tyr Ile Ile Asp Lys Glu
                405                 410                 415

Asp Ile Glu Leu Pro Ser Gly Lys Gln Glu Tyr Leu Ser Leu Leu
            420                 425                 430

Asn Ser Tyr Ile Val Lys Thr Ile Ala Glu Leu Arg
        435                 440

<210> SEQ ID NO 11
<211> LENGTH: 439
<212> TYPE: PRT
<213> ORGANISM: Haemophilus somnus

<400> SEQUENCE: 11

Met Ser Asn Tyr Phe Asp Lys Ile Ala Lys Val Asn Tyr Glu Gly Ala
1               5                   10                  15

Asn Ser Thr Asn Pro Phe Ala Phe Lys His Tyr Asn Pro Asn Glu Val
                20                  25                  30

Ile Leu Gly Lys Thr Val Glu Glu His Leu Arg Leu Ala Val Cys Tyr
            35                  40                  45

Trp His Thr Phe Cys Trp Thr Gly Asn Asp Met Phe Gly Ala Gly Ser
    50                  55                  60

Leu Asp Arg Ser Trp Gln Lys Thr Gly Asp Leu Leu Gly Ala Lys
65                  70                  75                  80

Gln Lys Ala Glu Ile Ala Phe Glu Phe Phe Gln Lys Leu Gly Val Pro
                85                  90                  95

Tyr Tyr Ser Phe His Asp Val Asp Ile Ala Pro Glu Ser Asn Asn Phe
            100                 105                 110

Lys Glu Tyr Leu His Asn Phe Asn Thr Ile Val Asp Ile Leu Glu Lys
        115                 120                 125

Lys Gln Ser Glu Thr Gly Val Lys Leu Leu Trp Gly Thr Ala Asn Cys
```

```
                    130                 135                 140
Phe Thr Asn Pro Arg Tyr Met Ser Gly Ala Ser Thr Asn Pro Asn Pro
145                 150                 155                 160

Glu Val Phe Ala Trp Ala Ala Gln Val Phe Thr Ala Met Asn Ala
                165                 170                 175

Thr Gln Arg Leu Gly Gly Glu Asn Tyr Val Leu Trp Gly Gly Arg Glu
                180                 185                 190

Gly Tyr Glu Thr Leu Leu Asn Thr Asp Leu Lys Arg Glu Arg Glu Gln
                195                 200                 205

Ile Gly Arg Phe Met Gln Leu Val Val Glu His Lys Tyr Lys Ile Gly
                210                 215                 220

Phe Gln Gly Thr Leu Leu Ile Glu Pro Lys Pro Gln Glu Pro Thr Lys
225                 230                 235                 240

His Gln Tyr Asp Tyr Asp Val Ala Thr Val Tyr Gly Phe Leu Lys Gln
                245                 250                 255

Phe Gly Leu Glu Asn Glu Ile Lys Val Asn Ile Glu Ala Asn His Ala
                260                 265                 270

Thr Leu Ala Gly His Thr Phe Gln His Glu Ile Ala Thr Ala Thr Ser
                275                 280                 285

Leu Gly Ile Phe Gly Ser Ile Asp Ala Asn Arg Gly Asp Pro Gln Leu
                290                 295                 300

Gly Trp Asp Thr Asp Gln Phe Pro Asn Ser Val Glu Glu Asn Thr Leu
305                 310                 315                 320

Ala Met Tyr Glu Ile Leu Lys Ala Gly Gly Phe Thr Thr Gly Gly Phe
                325                 330                 335

Asn Phe Asp Ala Lys Ile Arg Arg Gln Ser Thr Asp Pro Tyr Asp Leu
                340                 345                 350

Phe His Ala His Ile Gly Ala Met Asp Val Leu Ala Leu Ser Leu Lys
                355                 360                 365

Arg Ala Ala Lys Met Ile Glu Asp Gln Thr Leu Gln Lys Val Val Asp
                370                 375                 380

Asn Arg Tyr Ala Gly Trp Asp Gln Glu Leu Gly Gln Lys Ile Leu Asn
385                 390                 395                 400

Gly Lys Ala Ser Leu Glu Asp Leu Ala Lys Ile Val Glu Thr Gln Gly
                405                 410                 415

Leu Ala Pro Lys Pro Val Ser Gly Gln Gln Glu Tyr Leu Glu Asn Leu
                420                 425                 430

Val Asn Ser Tyr Leu Tyr Arg
                435

<210> SEQ ID NO 12
<211> LENGTH: 477
<212> TYPE: PRT
<213> ORGANISM: Arabidopsis thaliana

<400> SEQUENCE: 12

Met Lys Lys Val Glu Phe Phe Met Leu Leu Leu Cys Phe Ile Ala Ala
1               5                   10                  15

Ser Ser Leu Val Ser Ala Asp Pro Pro Thr Cys Pro Ala Asp Leu Gly
                20                  25                  30

Gly Lys Cys Ser Asp Ser Asp Asp Trp Gln Gly Asp Phe Phe Pro Glu
                35                  40                  45

Ile Pro Lys Ile Lys Tyr Glu Gly Pro Ser Ser Lys Asn Pro Leu Ala
                50                  55                  60
```

```
Tyr Arg Trp Tyr Asn Ala Glu Glu Ile Leu Gly Lys Lys Met Lys
 65                  70                  75                  80

Asp Trp Phe Arg Phe Ser Val Ala Phe Trp His Thr Phe Arg Gly Thr
                 85                  90                  95

Gly Gly Asp Pro Phe Gly Ala Ala Thr Lys Tyr Trp Pro Trp Glu Asp
                100                 105                 110

Gly Thr Asn Ser Val Ser Met Ala Lys Arg Arg Met Arg Ala Asn Phe
                115                 120                 125

Glu Phe Leu Lys Lys Leu Gly Val Asp Trp Trp Cys Phe His Asp Arg
            130                 135                 140

Asp Ile Ala Pro Asp Gly Thr Thr Leu Glu Glu Ser Asn Lys Asn Leu
145                 150                 155                 160

Asp Glu Val Ile Glu Leu Ala Lys Glu Leu Gln Lys Gly Ser Lys Ile
                165                 170                 175

Lys Pro Leu Trp Gly Thr Ala Gln Leu Phe Leu His Pro Arg Tyr Met
            180                 185                 190

His Gly Gly Ala Thr Ser Ser Glu Val Gly Val Tyr Ala Tyr Ala Ala
            195                 200                 205

Ala Gln Val Lys Lys Ala Met Glu Val Thr His Tyr Leu Gly Gly Glu
210                 215                 220

Asn Tyr Val Phe Trp Gly Gly Arg Glu Gly Tyr Gln Thr Leu Leu Asn
225                 230                 235                 240

Thr Asp Met Gly Arg Gly Leu Asp His Leu Ala Arg Phe Phe Glu Ala
                245                 250                 255

Ala Val Ala Tyr Lys Lys Lys Ile Gly Phe Lys Gly Thr Leu Leu Ile
            260                 265                 270

Glu Pro Lys Pro Gln Glu Pro Thr Lys His Gln Tyr Asp Trp Asp Ala
            275                 280                 285

Ala Thr Ala Ala Asn Phe Leu Arg Lys Tyr Gly Leu Ile Asp Glu Phe
290                 295                 300

Lys Leu Asn Ile Glu Cys Asn His Ala Thr Leu Ser Gly His Thr Cys
305                 310                 315                 320

His His Glu Leu Glu Thr Ala Arg Ile Asn Gly Leu Leu Gly Asn Ile
                325                 330                 335

Asp Ala Asn Thr Gly Asp Ala Gln Thr Gly Trp Asp Thr Asp Gln Phe
            340                 345                 350

Leu Thr Asp Val Gly Glu Ala Thr Met Val Met Met Ser Val Ile Lys
            355                 360                 365

Asn Gly Gly Ile Ala Pro Gly Gly Phe Asn Phe Asp Ala Lys Leu Arg
            370                 375                 380

Arg Glu Ser Thr Asp Val Glu Asp Leu Phe Ile Ala His Ile Ser Gly
385                 390                 395                 400

Met Asp Thr Met Ala Arg Gly Leu Arg Asn Ala Val Lys Ile Leu Glu
                405                 410                 415

Glu Gly Ser Leu Ser Glu Leu Val Arg Lys Arg Tyr Ala Thr Trp Asp
            420                 425                 430

Ser Glu Leu Gly Lys Gln Ile Glu Glu Gly Lys Ala Asp Phe Glu Tyr
            435                 440                 445

Leu Glu Lys Lys Ala Lys Glu Phe Gly Glu Pro Lys Val Ser Ser Ala
            450                 455                 460

Lys Gln Glu Leu Ala Glu Met Ile Phe Gln Ser Ala Met
465                 470                 475
```

<210> SEQ ID NO 13
<211> LENGTH: 479
<212> TYPE: PRT
<213> ORGANISM: Physcomitrella patens

<400> SEQUENCE: 13

| Met | Lys | Ala | Leu | Leu | Phe | Ser | Val | Val | Leu | Val | Ala | Val | Leu | Ser |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Cys | Ser | Gly | Gln | Arg | Val | Ala | Asp | Ile | Thr | Cys | Gly | Val | Asp | Gly | Ser |
|     |     |     | 20  |     |     |     |     | 25  |     |     |     |     | 30  |     |     |

Leu Gly Ser Asp Phe Gln Glu Trp Glu Gly Glu Phe Phe Pro Asn Ile
             35                  40                  45

Ser Tyr Ile Lys Tyr Glu Gly Pro Ala Ser His Asn Pro Leu Ala Tyr
 50                  55                  60

Lys Tyr Tyr Asn Ala Glu Glu Leu Ile Phe Gly Lys Lys Met Lys Asp
 65                  70                  75                  80

Trp Leu Arg Phe Ser Val Ala Phe Trp His Thr Phe Arg Gly Asp Gly
                 85                  90                  95

Gly Asp Pro Phe Gly Ser Pro Thr Lys Arg Trp Pro Trp Asp Asp Gly
             100                 105                 110

Ser Asn Ser Leu Thr Val Ala Val Arg Arg Met Arg Ala Asn Phe Glu
             115                 120                 125

Phe Leu Lys Lys Leu Gly Val Glu Lys Trp Cys Phe His Asp Arg Asp
130                 135                 140

Ile Ala Pro Glu Gly Ser Thr Leu Glu Glu Ser Asn Ala Asn Leu Asp
145                 150                 155                 160

Tyr Ile Val Ser Val Ala Lys Lys Leu Gln Glu Gly Thr Asn Ile Arg
                 165                 170                 175

Pro Leu Trp Gly Thr Ala Gln Leu Phe Lys His Pro Arg Tyr Met His
             180                 185                 190

Gly Ala Ala Thr Ser Pro Asp Val Arg Val Tyr Ala Tyr Ala Ala Ala
             195                 200                 205

Gln Val Lys Lys Ala Ile Glu Val Thr Lys Leu Leu Gly Gly Glu Asn
210                 215                 220

Tyr Val Phe Trp Gly Gly Arg Glu Gly Tyr Gln Thr Leu Leu Asn Thr
225                 230                 235                 240

Asp Leu Lys Lys Glu Leu Asp His Met Ala Thr Phe Leu Arg Ser Ala
                 245                 250                 255

Ala Glu Tyr Lys Lys Lys Ile Gly Phe Glu Gly Thr Leu Leu Leu Glu
             260                 265                 270

Pro Lys Pro Gln Glu Pro Thr Lys His Gln Tyr Asp Trp Asp Ala Ala
             275                 280                 285

Thr Thr Met Gly Phe Leu Lys Asn Tyr Gly Leu Ser Gly Thr Asn Asn
             290                 295                 300

Asp Tyr Lys Leu Asn Leu Glu Cys Asn His Ala Thr Leu Ser Gly His
305                 310                 315                 320

Ser Cys His His Glu Leu Glu Thr Ala Arg Ile Tyr Gly Met Leu Gly
                 325                 330                 335

Ser Val Asp Ala Asn Thr Gly Asp Ala Gln Thr Gly Trp Asp Thr Asp
             340                 345                 350

Gln Phe Leu Thr Asp Val Ser Glu Ala Thr Leu Ile Met Leu Ser Val
             355                 360                 365

Ile Lys Asn Gly Gly Leu Ala Pro Gly Gly Phe Asn Phe Asp Ala Lys
370                 375                 380

```
Leu Arg Arg Glu Ser Val Asp Val Glu Asp Leu Phe Ile Ala His Ile
385                 390                 395                 400

Ser Gly Met Asp Thr Ile Ala Arg Gly Leu Arg Asn Ala Ala Lys Leu
            405                 410                 415

Leu Glu Glu Gly Arg Leu Thr Lys Leu Val Glu Asp Arg Tyr Ser Ser
        420                 425                 430

Phe Asn Ser Pro Leu Gly Lys Thr Ile Glu Glu Gly Lys Val Gly Phe
            435                 440                 445

Glu Glu Leu Glu Lys Ile Ser Leu Glu Ala Glu Glu Pro Pro Ile Thr
        450                 455                 460

Ser Gly Lys Gln Glu Leu Ala Glu Met Ile Phe Tyr Ser Tyr Val
465                 470                 475

<210> SEQ ID NO 14
<211> LENGTH: 20
<212> TYPE: DNA
<213> ORGANISM: Artificial
<220> FEATURE:
<223> OTHER INFORMATION: forward degenerate primer

<400> SEQUENCE: 14
ttytggggwg ghmgdgargg                                              20

<210> SEQ ID NO 15
<211> LENGTH: 20
<212> TYPE: DNA
<213> ORGANISM: Artificial
<220> FEATURE:
<223> OTHER INFORMATION: reverse degenerate primer
<220> FEATURE:
<221> NAME/KEY: misc_feature
<222> LOCATION: (9)..(9)
<223> OTHER INFORMATION: n is a, c, g, or t

<400> SEQUENCE: 15
aaytsrtcng trtcccadcc                                              20

<210> SEQ ID NO 16
<211> LENGTH: 1352
<212> TYPE: DNA
<213> ORGANISM: Clostridium difficile

<400> SEQUENCE: 16
tctagaaaat gaacgaaatc ttcaagggta tcggtcaaat caagttcgaa ggtgttaagt    60
ctaacaacga attggctttc agatactaca acccagaaca agttgttggt aacaagacca   120
tgaaggaaca cttgagattc gctatgtctt actggcacac cttgtgtggt gaaggtaacg   180
acccattcgg tgttggtact gttgaaagac cttggaacaa catcaccgac ccaatcgaaa   240
tcgctaagat caaggttgac gctggtttcg aatttatgtc taagatgggt atcgaatact   300 tctgttttcca cgacagagac atcgctccag aaggtagaga cttggaagaa ccaacaaga   360 tcttggacga aatcgttgaa tacatcaagg ctaacatgga aaagactggt atcaagttgt   420
tgtggggtac tgctaacatg ttcggtaacc caagattcgt tcacggtgct tctaccacct   480
gtaacgctga cgtttacgct tacgctgctg ctcaagttaa aaggctatg gaaatcacca   540 agtacttggg tggtgaaaac ttcgttttct ggggtggtag agaaggttac gaaaccttgt   600
tgaacaccaa caccgaattg gaaatggaca cttcgctag attcttgcaa atggctgttg   660
actacgctaa ggaaatcggt ttcactggtc aattcttgat cgaaccaaag ccaaaggaac   720
caaccaagca ccaatacgac ttcgacaccg ctaccgtttt gggtttcttg agaaagtaca   780
```

```
acttggacaa gtacttcaag gttaacatcg aagctaacca cgctaccttg gctggtcaca      840
ccttccaaca cgaattgaac atcgctagaa tcaacaacgt tttgggttct atcgacgcta      900
accaaggtga cttgttgttg ggttgggaca ccgaccaatt cccaaccaac atctacgacg      960
ctaccttggc tatgtacgaa gttttgaagc aaggtggtat cgctccaggt ggtttcaact     1020
tcgactctaa ggttagaaga gcttctttcg aagttgaaga cttgttcttg gcttacatcg     1080
ctggtatgga caccttcgct aagggtttgt tgatcgctca caagttgttg gaagacgaag     1140
ttttcgaaaa cttcaccaag gaaagatacg cttctttctc tgaaggtatc ggtaaggaca     1200
tcgttgaagg taaggttggt ttcaaggaat tggaatctta cgctttgcaa atgccagtta     1260
tcaagaacaa gtctggtaga caagaaatgt tggaagctat cttgaacaga tacatctacg     1320
aagttgacac catctctaac aagtaaggat cc                                   1352

<210> SEQ ID NO 17
<211> LENGTH: 1385
<212> TYPE: DNA
<213> ORGANISM: Ciona intestinalis

<400> SEQUENCE: 17
tctagaaaat gtcttctttc gctccagctt ctggtaagtc tgacttggct gaagctggtt       60
ctttgttgac caagtaccca ttggaagtta agaagatccc atacaagcca gacgctaagg      120
ttgacgacgt tttgtgtttc agacactaca acgaatctga agttgttatg ggtaagccaa      180
tgtctgactg gttgagattc tctgtttgtt actggcacac cttcagaggt accggtgctg      240
acccattcgg tttcccaacc ttggttagac cttgggacga cggtaccgac tctatcgaaa      300
acgctgaaag aagaatgaga gttgcttttcg acttcatgtc taagttgggt gttaagtact      360
ggaccttcca cgacagagac atcgctccag aaggtgttac cttgtctgaa accaacgcta      420
acttggacag attggctgaa ttggcttctc aattgcaagg tgaaaccggt atcaagttgt      480
tgtggaacac ctgtaacttg ttcgctcacc caagatactc taacggtgct gctaccaacg      540
ctgacgctca cgttgttgct tacgctgctc tcaagttaa gaagtctttg gaatccggta      600
agaagttggg tgctgaaaac ttcgtttttct ggggtggtag agaaggttac cacaccttgt      660
tgaacaccaa cgttagagaa gaattggaca cttggctaa cttcttcaag atggttgttg      720
cttacaagaa gaagatcggt ttcaccggtc aattcttgat cgaaccaaag ccaaaggaac      780
catctaagca ccaatacgac tacgacgcta tgaccgttat cgctttcttg aagacctacg      840
acttggacaa ggacttcaag ttgaacatcg aaccaaacca caccaccttg gctggtcact      900
gtcacgaaca cgacgttgtt atggcttctg cttacaacat gttgggttct gttgactcta      960
acaccggttc tccagacttg ggttgggaca ccgaccaatt cccaatggac gttaagaacg     1020
ctaccatgat catgcaaacc gttttggaac aaggtggttt ggctccaggt ggtttgaact     1080
tcgactgtaa ggttagaaga gaatctaccg acgttatcga catgatgatc gctcacgttg     1140
gtgctatgga ctgtttcgct aaggctttga agatcgctgc taagatcaga gaagacggtg     1200
ttttgggtaa gatgaagaag gaaagatacg cttctttcgg ttctggtttg ggtttgaaga     1260
tcaagaccgg taccgctacc ttgaagaat gtgactcttt catccaagaa aacggtgaac     1320
cagctaagtt gtctggtaag caagaaatgt tcgaagctgt tttgaacaga tacttctaag     1380
gatcc                                                                 1385

<210> SEQ ID NO 18
```

<211> LENGTH: 1314
<212> TYPE: DNA
<213> ORGANISM: Piromyces sp.

<400> SEQUENCE: 18

```
atggctaagg aatacttccc acaaatccaa aagatcaagt tcgaaggtaa ggactctaag      60
aacccattgg ctttccacta ctacgacgct gaaaaggaag ttatgggtaa gagatgaag     120
gactggttga gattcgctat ggcttggtgg cacaccttgt gtgctgaagg tgctgaccaa    180
ttcggtggtg gtaccaagtc tttcccatgg aacgaaggta ccgacgctat cgaaatcgct    240
aagcaaaagg ttgacgctgg tttcgaaatc atgcaaaagt tgggtatccc atactactgt    300
ttccacgacg tcgacttggt ttctgaaggt aactctatcg aagaatacga atctaacttg    360
aaggctgttg ttgcttactt gaaggaaaag caaaaggaaa ctggtatcaa gttgttgtgg    420
tctaccgcta acgttttcgg tcacaagaga tacatgaacg gtgcttctac caacccagac    480
ttcgacgttg ttgctagagc tatcgttcaa atcaagaacg ctatcgacgc tggtatcgaa    540
ttgggtgctg aaaactacgt tttctggggt ggtagagaag gttacatgtc tttgttgaac    600
accgaccaaa agagagaaaa ggaacacatg gctaccatgt tgaccatggc tagagactac    660
gctagatcta agggtttcaa gggtaccttc ttgatcgaac aaagccaat ggaaccaacc     720
aagcaccaat acgacgttga caccgaaacc gctatcggtt tcttgaaggc tcacaacttg    780
gacaaggact tcaaggtcaa catcgaagtt aaccacgcta ccttggctgg tcacaccttc    840
gaacacgaat ggcttgtgc tgttgacgct ggtatgttgg ttctatcga cgctaacaga     900
ggtgactacc aaaacggttg gacaccgac caattcccaa tcgaccaata cgaattggtt     960
caagcctgga tggaaatcat cagaggtggt ggtttcgtta ctggtggtac caacttcgac   1020
gctaagacca aagaaactc taccgacttg aagacatca tcatcgctca cgtttctggt    1080
atggacgcta tggctagagc tttggaaaac gctgctaagt tgttgcaaga atctccatac   1140
accaagatga agaaggaaag atacgcttct ttcgactctg gtatcggtaa ggacttcgaa   1200
gacggtaagt tgaccttgga acaagtttac gaatacggta agaagaacgg tgaaccaaag   1260
caaacctctg gtaagcaaga attgtacgaa gctatcgttg ctatgtacca ataa          1314
```

<210> SEQ ID NO 19
<211> LENGTH: 1328
<212> TYPE: DNA
<213> ORGANISM: Cyllamyces aberensis

<400> SEQUENCE: 19

```
tctagaaaat ggttaaggaa tacttcccag ctatccaaaa gatcaagttc gaaggtaagg      60
actctaagaa cccaatggct ttccactact acgacgctga aaaggaaatc atgggtaaga    120
agatgaagga ctggttgaga ttcgctatgg cttggtggca ccttgtgt gctgaaggtt      180
ctgaccaatt cggtccaggt accaagacct cccttggaa cgaaggtacc gacccaatcg    240
aaaaggctaa gcaaaaggtt gacgctggtt tcgaaatcat gaccaagttg ggtatcgaac    300
actactgttt ccacgacgtt gacttggttg acgaaggtaa aacgttgaa gaatacgaaa    360
agaacttgaa gaccatcgtt gcttacttga aggaaaagca aaaggaaact ggtatcaagt    420
tgttgtggtc taccgctaac gttttcggtc acaagagata catgaacggt gcttctacca    480
acccagactt cgacgttgtt gctagagcta tcgttcaaat caagaacgct atggacgctg    540
gtatcgaatt gggtgctgaa aactacgttt tctggggtgg tagagaaggt tacatgtctt    600
tgttgaacac cgaccaaaag agagaaaagg aacacatggc tatgatgttg ggtttggcta    660
```

-continued

| | |
|---|---|
| gagactacgc tagatctaag ggtttcaagg gtaccttctt gatcgaacca aagccaatgg | 720 |
| aaccaaccaa gcaccaatac gacgttgaca ccgaaaccgt tatcggtttc ttgagagctc | 780 |
| acggtttgga caaggacttc aagatcaaca tcgaagttaa ccacgctacc ttggctggtc | 840 |
| acaccttcga acacgaattg gcttgtgctg ttgacgctgg tatgttgggt tctatcgacg | 900 |
| ctaacagagg tgactaccaa aacggttggg acaccgacca attcccaatc gaccaatacg | 960 |
| aattggttca agcctggatg gaaatcatca gaggtggtgg tttcaccact ggtggtacca | 1020 |
| acttcgacgc taagaccaga agaaactcta ccgacttgga agacatcatc atcgctcaca | 1080 |
| tctctggtat ggacgctatg gctagagctt tggaaaacgc tgctaagttg ttgaccgaat | 1140 |
| ctccatacaa gaagatgaag gctgacagat acgcttcttt cgactctggt atgggtaagg | 1200 |
| acttcgaaga cggtaagttg accttcgaac aagtttacga atacggtaag aaggttaacg | 1260 |
| aaccaaagca aacctctggt aagcaagaat tgtacgaagc tatcgttgct atgtacatgt | 1320 |
| aaggatcc | 1328 |

<210> SEQ ID NO 20
<211> LENGTH: 1334
<212> TYPE: DNA
<213> ORGANISM: Bacteroides fragilis

<400> SEQUENCE: 20

| | |
|---|---|
| tctagaaaat ggctaccaag gaatacttcc caggtatcgg taagatcaag ttcgaaggta | 60 |
| aggactctaa gaacccaatg gctttcagat actacgacgc tgaaaagatg atcaacggta | 120 |
| gatctatgaa ggactggttg aagttcgcta tggcttggtg gcacaccttg tgtgctgaag | 180 |
| gtggtgacca attcggtggt ggtaccaagc aattccttg gaacggtgac ccagacccag | 240 |
| ttcaagctgc taagaacaag atggacgctg gtttcgaatt tatgcaaaag atgggtatcg | 300 |
| gttactactg tttccacgac gttgacttgg ttaccgaagc tgactctatc gaagcctacg | 360 |
| aagctaactt gaaggaattg gttgcttacg ctaagcaaaa gcaagctgaa actggtatca | 420 |
| agttgttgtg gggtactgct aacgttttct ctcacgctag atacatgaac ggtgctgcta | 480 |
| ccaacccaga cttcgacgtt gttgctagag ctgctgttca aatcaagaac gctatcgacg | 540 |
| ctaccatcga attgggtggt accaactacg ttttctgggg tggtagagaa ggttacatgt | 600 |
| ctttgttgaa caccgaccaa aagagagaaa aggaacactt ggctcaaatg ttgaccatcg | 660 |
| ctagagacta cggtagagct agaggtttca agggtacttt cttgatcgaa ccaaagccaa | 720 |
| tggaaccaac caagcaccaa tacgacgttg acaccgaaac cgttatcggt ttcttgaagg | 780 |
| ctcacggttt gaaccaagac ttcaaggtta acatcgaagt taaccacgct accttggctg | 840 |
| gtcacacctt cgaacacgaa ttggctgttg ctgttgacaa cggtatgttg ggttctatcg | 900 |
| acgctaacag aggtgactac caaaacggtt gggacaccga ccaattccca atcgacaact | 960 |
| tcgaattgac ccaagctatg atgcaaatca tcagaacga cggttgggt aacggtggta | 1020 |
| ccaacttcga cgctaagacc agaagaaact ctaccgaccc agaagacatc ttcatcgctc | 1080 |
| acatcgctgg tatggacgct atggctagag ctttggaatc tgctgctaac ttgttgaacg | 1140 |
| aatctccata ccaaaagatg ttgtctgaca gatacgcttc tttcgacgct ggtaagggta | 1200 |
| aggaatttga agaaggtaag ttgtctttgg aagaattggt tgcttacgct aaggctaacg | 1260 |
| gtgaaccaaa gcaaacctct ggtcaacaag aattgtacga agccttggtt aacatctact | 1320 |
| ctttgtaagg atcc | 1334 |

<210> SEQ ID NO 21
<211> LENGTH: 1337
<212> TYPE: DNA
<213> ORGANISM: Burkholderia phytofirmans

<400> SEQUENCE: 21

| | | | | | |
|---|---|---|---|---|---|
| tctagaaaat | gtcttacttc | gaacacatcc | cagaaatcag | atacgaaggt | ccacaatctg | 60 |
| acaacccatt | ggcttacaga | cactacgaca | agtctaagaa | ggttttgggt | aagaccttgg | 120 |
| aagaacactt | gagaatcgct | gtttgttact | ggcacacctt | cgtttggcca | ggtgttgaca | 180 |
| tcttcggtca | aggtaccttc | agaagacctt | ggcaacaagc | tggtgacgct | atggaaagag | 240 |
| ctcaacaaaa | ggctgactct | gctttcgaat | ttttctctaa | gttgggtacc | ccatactaca | 300 |
| ccttccacga | caccgacgtt | ctccagaag | gttctaactt | gaaggaatac | tctgaaaact | 360 |
| tcttgagaat | caccgactac | ttggctagaa | agcaagaatc | tactggtatc | aagttgttgt | 420 |
| ggggtaccgc | taacttgttc | tctcacccaa | gatacgctgc | tggtgctgct | acctctccag | 480 |
| acccagaagt | tttcgctttc | gctgctaccc | aagttagaca | cgctttggac | gctacccaaa | 540 |
| gattgggtgg | tgacaactac | gttttgtggg | gtggtagaga | aggttacgac | accttgttga | 600 |
| acaccgactt | ggttagagaa | agagaccaat | tggctagatt | cttgcacatg | gttgttgacc | 660 |
| acgctcacaa | gatcggtttc | aagggttctt | tgttgatcga | accaaagcca | caagaaccaa | 720 |
| ccaagccacca | atacgactac | gacgttgcta | ccgttcacgg | tttcttgttg | caacacggtt | 780 |
| tggacaagga | aatcagagtt | aacatcgaag | ctaaccacgc | taccttggct | ggtcactctt | 840 |
| tccaccacga | aatcgctacc | gcttacgctt | gggtatcttc | ggttctgtt | gacgctaaca | 900 |
| gaggtgaccc | acaaaacggt | tgggacaccg | accaattccc | aaactctgtt | gaagaattga | 960 |
| ccttggcttt | ctacgaaatc | ttgaagcacg | gtggtttcac | cactggtggt | atgaacttcg | 1020 |
| actctaaggt | tagaagacaa | tctgttgacc | agaagactt | gttctacggt | cacatcggtg | 1080 |
| ctatcgacaa | cttggctttg | gctgttaaa | gagctgctgt | tttgatcgaa | aacgacagat | 1140 |
| tggaccaatt | caagagacaa | agatactctg | gttgggacgc | tgaatttggt | agaaagatct | 1200 |
| cttctggtga | ctactctttg | tctgctttgg | ctgaagaagc | tatggctaga | ggtttgaacc | 1260 |
| cacaacacgc | ttctggtcac | caagaattga | tggaaaacat | cgttaaccaa | gctatctact | 1320 |
| ctggtagata | aggatcc | | | | | 1337 |

<210> SEQ ID NO 22
<211> LENGTH: 1202
<212> TYPE: DNA
<213> ORGANISM: Arthrobacter aurescens

<400> SEQUENCE: 22

| | | | | | |
|---|---|---|---|---|---|
| tctagaaaat | gaccccacaa | ccaaccccac | aagacagatt | caccttcggt | ttgtggaccg | 60 |
| ttggttggac | cggtgctgac | ccattcggtg | ttgctaccag | accagctttg | gacccagttg | 120 |
| aagctgttca | caagttgtct | gaattgggtg | cttacggtat | caccttccac | gacaacgact | 180 |
| tggttccatt | cgacgctacc | gcttctgaaa | gagacttgat | cttgaagaac | ttcaaggctg | 240 |
| ctttggctga | aaccgttttg | aagacccaa | tggttaccac | caacttgttc | tctcacccag | 300 |
| ttttcaagga | cggtggtttc | acctctaacg | acagatctat | cagaagattc | gctttgtcta | 360 |
| agatcttgag | aaacatcgac | ttggctgctg | aattgggtgc | tgaaaccttc | gttatgtggg | 420 |
| gtggtagaga | aggttctgaa | tacgacggtt | ctaaggactt | gtctgctgct | ttggacagaa | 480 |
| tgaaggaagg | tgttgacacc | gctgctggtt | acatcaagga | aaagggttac | ggtttgagaa | 540 |

```
tcgctttgga accaaagcca aacgaaccaa gaggtgacat cttcttgcca accgttggtc      600
acggtttggc tttcatcgct caattggaac acggtgacat cgttggtttg aacccagaaa      660
ccggtcacga acaaatggct ggtttgaact tcacccacgg tatcgctcaa gccttgtggg      720
ctggtaagtt gttccacatc gacttgaacg gtcaaagagg tatcaagtac gaccaagact      780
tggttttcgg tcacggtgac ttgacctctg cttctcttcac cgttgacttg ttggaaaacg      840
gtttcccaaa cggtggtcca agtacgacg gtccaagaca cttcgactac aagccatcca       900
gaaccgacgg ttacgacggt gtttgggaat ctgctaagtc taacatgtct atgtacttgt      960
tgttgaagga aagagctttg gctttcagag ctgacccaga agttcaagaa gccttggcta     1020
cctctggtgt tttcgaattg ggtgaaccaa ccttgaacgc tggtgaaacc accgctgact     1080
tgttggctga cgcttctgct ttcgacacct caacgctga ccaagctgct gaaagatctt      1140
tcgctttcgt tagattgaac caattagcta tcgaacactt gttgggtgct agataaggat     1200
cc                                                                    1202

<210> SEQ ID NO 23
<211> LENGTH: 1349
<212> TYPE: DNA
<213> ORGANISM: Thermotoga maritima

<400> SEQUENCE: 23
tctagaaaat ggctgaattt ttcccagaaa tcccaaagat ccaattcgaa ggtaaggaat       60
ctaccaaccc attggctttc agattctacg acccaaacga agttatcgac ggtaagccat      120
tgaaggacca cttgaagttc tctgttgctt tctggcacac cttcgttaac gaaggtagag      180
acccattcgg tgacccaacc gctgaaagac cttggaacag attctctgac ccaatggaca      240
aggctttcgc tagagttgac gcttttgttcg aattttgtga aaagttgaac atcgaatact      300
tctgtttcca cgacagagac atcgctccag aaggtaagac cttgagagaa ccaacaagaa      360
tcttggacaa ggttgttgaa agaatcaagg aaagaatgaa ggactctaac gttaagttgt      420
tgtggggtac tgctaacttg ttctctcacc caagatacat gcacggtgct gctaccacct      480
gttctgctga cgtttttcgct tacgctgctg ctcaagttaa gaaggctttg gaaatcacca      540
aggaattggg tggtgaaggt tacgttttct ggggtggtag agaaggttac gaaaccttgt      600
tgaacaccga cttgggtttg gaattggaaa acttggctag attcttgaga atggctgttg      660
aatacgctaa gaagatcggt ttcactggtc aattcttgat cgaaccaaag ccaaaggaac      720
caaccaagca ccaatacgac ttcgacgttg ctaccgcttg cgctttcttg aagaaccacg      780
gtttggacga atacttcaag ttcaacatcg aagctaacca cgctaccttg gctggtcaca      840
ccttccaaca cgaattgaga atggctgaaa tcttgggtaa gttgggttct atcgacgcta      900
accaaggtga cttgttgttg ggttgggaca ccgaccaatt cccaaccaac atctacgaca      960
ccaccttggc tatgtacgaa gttatcaagg ctggtggttt caccaagggt ggtttgaact     1020
tcgacgctaa ggttagaaga gcttcttaca aggttgaaga cttgttcatc ggtcacatcg     1080
ctggtatgga caccttcgct ttgggtttca gatcgctta caagttggct aaggacggtg      1140
ttttcgacaa gttcatcgaa gaaagtaca gatctttcaa ggaaggtatc ggtaaggaaa      1200
tcgttgaagg taagaccgac ttcgaaaagt tggaagaata catcatcgac aaggaagaca     1260
tcgaattgcc atctggtaag caagaatact tggaatcttt gttgaactct tacatcgtta     1320
agaccatcgc tgaattgaga taaggatcc                                       1349
```

<210> SEQ ID NO 24
<211> LENGTH: 1334
<212> TYPE: DNA
<213> ORGANISM: Haemophilus somnus

<400> SEQUENCE: 24

| | | | | |
|---|---|---|---|---|
| tctagaaaat | gtctaactac | ttcgacaaga | tcgctaaggt | taactacgaa | ggtgctaact | 60 |
| ctaccaaccc | attcgctttc | aagcactaca | acccaaacga | agttatcttg | ggtaagaccg | 120 |
| ttgaagaaca | cttgagattg | gctgtttgtt | actggcacac | cttctgttgg | accggtaacg | 180 |
| acatgttcgg | tgctggttct | ttggacagat | cttggcaaaa | gaccggtgac | ttgttggttg | 240 |
| gtgctaagca | aaaggctgaa | atcgctttcg | aattcttcca | aaagttgggt | gttccatact | 300 |
| actctttcca | cgacgttgac | atcgctccag | aatctaacaa | cttcaaggaa | tacttgcaca | 360 |
| acttcaacac | catcgttgac | atcttggaaa | agaagcaatc | tgaaaccggt | gttaagttgt | 420 |
| tgtggggtac | tgctaactgt | ttcaccaacc | aagatacat | gtctggtgct | tctaccaacc | 480 |
| caaacccaga | agttttcgct | tgggctgctg | ctcaagtttt | caccgctatg | aacgctaccc | 540 |
| aaagattggg | tggtgaaaac | tacgttttgt | ggggtggtag | agaaggttac | gaaaccttgt | 600 |
| tgaacaccga | cttgaagaga | aaagagaac | aaatcgtag | attcatgcaa | ttggttgttg | 660 |
| aacacaagta | caagatcggt | ttccaaggta | ccttgttgat | cgaaccaaag | ccacaagaac | 720 |
| caaccaagca | ccaatacgac | tacgacgttg | ctaccgttta | cggtttcttg | aagcaattcg | 780 |
| gtttggaaaa | cgaaatcaag | gttaacatcg | aagctaacca | cgctaccttg | gctggtcaca | 840 |
| ccttccaaca | cgaaatcgct | accgctacct | ctttgggtat | cttcggttct | atcgacgcta | 900 |
| acagaggtga | cccacaattg | ggttgggaca | ccgaccaatt | cccaaactct | gttgaagaaa | 960 |
| acaccttggc | tatgtacgaa | atcttgaagg | ctggtggttt | caccaccggt | ggtttcaact | 1020 |
| tcgacgctaa | gatcagaaga | caatctaccg | acccatacga | cttgttccac | gctcacatcg | 1080 |
| gtgctatgga | cgttttggct | ttgtctttga | agagagctgc | taagatgatc | gaagaccaaa | 1140 |
| ccttgcaaaa | ggttgttgac | aacagatacg | ctggttggga | ccaagaattg | ggtcaaaaga | 1200 |
| tcttgaacgg | taaggcttct | ttggaagact | tggctaagat | cgttgaaacc | caaggtttgg | 1260 |
| ctccaaagcc | agtttctggt | caacaagaat | acttggaaaa | cttggttaac | tcttacttgt | 1320 |
| acagataagg | atcc | | | | | 1334 |

<210> SEQ ID NO 25
<211> LENGTH: 1448
<212> TYPE: DNA
<213> ORGANISM: Arabidopsis thaliana

<400> SEQUENCE: 25

| | | | | |
|---|---|---|---|---|
| tctagaaaat | gaagaaggtt | gaattcttca | tgttgttgtt | gtgtttcatc | gctgcttctt | 60 |
| ctttggtttc | tgctgaccca | ccaacctgtc | cagctgactt | gggtggtaag | tgttctgact | 120 |
| ctgacgactg | gcaaggtgac | ttcttcccag | aaatcccaaa | gatcaagtac | gaaggtccat | 180 |
| cttctaagaa | cccattggct | tacagatggt | acaacgctga | agaagaaatc | ttgggtaaga | 240 |
| agatgaagga | ctggttcaga | ttctctgttg | ctttctggca | caccttcaga | ggtaccggtg | 300 |
| gtgacccatt | cggtgctgct | accaagtact | ggccatggga | agacggtacc | aactctgttt | 360 |
| ctatggctaa | gaagaagaatg | agagctaact | tcgaattctt | gaagaagttg | ggtgttgact | 420 |
| ggtggtgttt | tccacgacaga | gacatcgctc | cagacggtac | caccttggaa | gaatctaaca | 480 |
| agaacttgga | cgaagttatc | gaattggcta | aggaattgca | aaagggttct | aagatcaagc | 540 |

```
cattgtgggg taccgctcaa ttgttcttgc acccaagata catgcacggt ggtgctacct      600
cttctgaagt tggtgtttac gcttacgctg ctgctcaagt taagaaggct atggaagtta      660
cccactactt gggtggtgaa aactacgttt tctggggtgg tagagaaggt taccaaacct      720
tgttgaacac cgacatgggt agaggtttgg accacttggc tagattcttc gaagctgctg      780
ttgcttacaa gaagaagatc ggtttcaagg gtaccttgtt gatcgaacca aagccacaag      840
aaccaaccaa gcaccaatac gactgggacg ctgctaccgc tgctaacttc ttgagaaagt      900
acggtttgat cgacgaattc aagttgaaca tcgaatgtaa ccacgctacc ttgtctggtc      960
acacctgtca ccacgaattg gaaaccgcta gaatcaacgg tttgttgggt aacatcgacg     1020
ctaacaccgg tgacgctcaa accggttggg acaccgacca attcttgacc gacgttggtg     1080
aagctaccat ggttatgatg tctgttatca agaacggtgg tatcgctcca ggtggtttca     1140
acttcgacgc taagttgaga agagaatcta ccgacgttga agacttgttc atcgctcaca     1200
tctctggtat ggacaccatg gctagaggtt tgagaaacgc tgttaagatc ttggaagaag     1260
gttctttgtc tgaattggtt agaaagagat acgctacctg ggactctgaa ttgggtaagc     1320
aaatcgaaga aggtaaggct gacttcgaat acttggaaaa gaaggctaag gaattcggtg     1380
aaccaaaggt ttcttctgct aagcaagaat tggctgaaat gatcttccaa tctgctatgt     1440
aaggatcc                                                              1448

<210> SEQ ID NO 26
<211> LENGTH: 1454
<212> TYPE: DNA
<213> ORGANISM: Physcomitrella patens

<400> SEQUENCE: 26
tctagaaaat gaaggctttg ttgttctctg ttgttttgtt ggttgctgtt ttgtcttgtt       60
ctggtcaaag agttgctgac atcacctgtg gtgttgacgg ttctttgggt tctgacttcc      120
aagaatggga aggtgaattt ttcccaaaca tctcttacat caagtacgaa ggtccagctt      180
ctcacaaccc attggcttac aagtactaca acgctgaaga attgatcttc ggtaagaaga      240
tgaaggactg gttgagattc tctgttgctt tctggcacac cttcagaggt gacggtggtg      300
acccattcgg ttctccaacc aagagatggc cttgggacga cggttctaac tctttgaccg      360
ttgctgttag aagaatgaga gctaacttcg aattcttgaa gaagttgggt gttgaaaagt      420 ggtgttttcca cgacagagac atcgctccag aaggttctac cttggaagaa tctaacgcta      480
acttggacta catcgtttct gttgctaaga agttgcaaga aggtaccaac atcagaccat      540 tgtgggggtac cgctcaattg ttcaagcacc aagatacat gcacggtgct gctacctctc      600
cagacgttag agtttacgct tacgctgctg ctcaagttaa gaaggctatc gaagttacca      660
agttgttggg tggtgaaaac tacgtttttct ggggtggtag agaaggttac caaaccttgt      720
tgaacaccga cttgaagaag gaattggacc acatggctac cttcttgaga tctgctgctg      780
aatacaagaa gaagatcggt ttcgaaggta ccttgttgtt ggaaccaaag ccacaagaac      840
caaccaagca ccaatacgac tgggacgctg ctaccactat gggtttcttg aagaactacg      900
gtttgtctgg taccaacaac gactacagt tgaacttgga atgtaaccac gctaccttgt      960
ctggtcactc ttgtcaccac gaattggaaa ccgctagaat ctacggtatg ttgggttctg     1020
ttgacgctaa cactggtgac gctcaaactg gtttgggacac cgaccaattc ttgaccgacg     1080
tttctgaagc taccttgatc atgttgtctg ttatcaagaa cggtggtttg gctccaggtg     1140
```

```
gtttcaactt cgacgctaag ttgagaagag aatctgttga cgttgaagac ttgttcatcg   1200
ctcacatctc tggtatggac accatcgcta gaggtttgag aaacgctgct aagttgttgg   1260
aagaaggtag attgaccaag ttggttgaag acagatactc ttctttcaac tctccattgg   1320
gtaagaccat cgaagaaggt aaggttggtt tcgaagaatt ggaaaagatc tctttggaag   1380
ctgaagaacc accaatcacc tctggtaagc aagaattggc tgaaatgatc ttctactctt   1440
acgtttaagg atcc                                                    1454
```

<210> SEQ ID NO 27
<211> LENGTH: 6
<212> TYPE: PRT
<213> ORGANISM: Piromyces sp.

<400> SEQUENCE: 27

Thr Gly Ile Lys Leu Leu
1               5

<210> SEQ ID NO 28
<211> LENGTH: 5
<212> TYPE: PRT
<213> ORGANISM: Piromyces sp.

<400> SEQUENCE: 28

Thr Leu Ala Gly His
1               5

<210> SEQ ID NO 29
<211> LENGTH: 5
<212> TYPE: PRT
<213> ORGANISM: Piromyces sp.

<400> SEQUENCE: 29

Arg Tyr Ala Ser Phe
1               5

<210> SEQ ID NO 30
<211> LENGTH: 511
<212> TYPE: PRT
<213> ORGANISM: Arthrobacter aurescens
<220> FEATURE:
<221> NAME/KEY: misc_feature
<223> OTHER INFORMATION: araA

<400> SEQUENCE: 30

Met Pro Ser Ala Thr Ser Asn Pro Ala Asn Asn Thr Ser Leu Glu Gln
1               5                   10                  15

Tyr Glu Val Trp Phe Leu Thr Gly Ser Gln His Leu Tyr Gly Glu Asp
                20                  25                  30

Val Leu Lys Gln Val Ala Ala Gln Ser Gln Glu Ile Ala Asn Ala Leu
            35                  40                  45

Asn Ala Asn Ser Asn Val Pro Val Lys Leu Val Trp Lys Pro Val Leu
        50                  55                  60

Thr Asp Ser Asp Ala Ile Arg Arg Thr Ala Leu Glu Ala Asn Ala Asp
65                  70                  75                  80

Asp Ser Val Ile Gly Val Thr Ala Trp Met His Thr Phe Ser Pro Ala
                85                  90                  95

Lys Met Trp Ile Gln Gly Leu Asp Ala Leu Arg Lys Pro Leu Leu His
                100                 105                 110

Leu His Thr Gln Ala Asn Arg Asp Leu Pro Trp Ala Asp Ile Asp Phe
            115                 120                 125

Asp Phe Met Asn Leu Asn Gln Ala Ala His Gly Asp Arg Glu Phe Gly
    130                 135                 140

Tyr Ile Gln Ser Arg Leu Gly Val Pro Arg Lys Thr Val Val Gly His
145                 150                 155                 160

Val Ser Asn Pro Glu Val Ala Arg Gln Val Gly Ala Trp Gln Arg Ala
                165                 170                 175

Ser Ala Gly Trp Ala Ala Val Arg Thr Leu Lys Leu Thr Arg Phe Gly
            180                 185                 190

Asp Asn Met Arg Asn Val Ala Val Thr Glu Gly Asp Lys Thr Glu Ala
        195                 200                 205

Glu Leu Arg Phe Gly Val Ser Val Asn Thr Trp Ser Val Asn Glu Leu
210                 215                 220

Ala Asp Ala Val His Gly Ala Ala Glu Ser Asp Val Asp Ser Leu Val
225                 230                 235                 240

Ala Glu Tyr Glu Arg Leu Tyr Glu Val Val Pro Glu Leu Lys Lys Gly
                245                 250                 255

Gly Ala Arg His Glu Ser Leu Arg Tyr Ser Ala Lys Ile Glu Leu Gly
            260                 265                 270

Leu Arg Ser Phe Leu Glu Ala Asn Gly Ser Ala Ala Phe Thr Thr Ser
        275                 280                 285

Phe Glu Asp Leu Gly Ala Leu Arg Gln Leu Pro Gly Met Ala Val Gln
290                 295                 300

Arg Leu Met Ala Asp Gly Tyr Gly Phe Gly Ala Glu Gly Asp Trp Lys
305                 310                 315                 320

Thr Ala Ile Leu Val Arg Ala Ala Lys Val Met Gly Gly Asp Leu Pro
                325                 330                 335

Gly Gly Ala Ser Leu Met Glu Asp Tyr Thr Tyr His Leu Glu Pro Gly
            340                 345                 350

Ser Glu Lys Ile Leu Gly Ala His Met Leu Glu Val Cys Pro Ser Leu
        355                 360                 365

Thr Ala Lys Lys Pro Arg Val Glu Ile His Pro Leu Gly Ile Gly Gly
370                 375                 380

Lys Glu Asp Pro Val Arg Met Val Phe Asp Thr Asp Ala Gly Pro Gly
385                 390                 395                 400

Val Val Val Ala Leu Ser Asp Met Arg Asp Arg Phe Arg Leu Val Ala
                405                 410                 415

Asn Val Val Asp Val Asp Leu Asp Gln Pro Leu Pro Asn Leu Pro
            420                 425                 430

Val Ala Arg Ala Leu Trp Glu Pro Lys Pro Asn Phe Ala Thr Ser Ala
        435                 440                 445

Ala Ala Trp Leu Thr Ala Gly Ala Ala His His Thr Val Leu Ser Thr
450                 455                 460

Gln Val Gly Leu Asp Val Phe Glu Asp Phe Ala Glu Ile Ala Lys Thr
465                 470                 475                 480

Glu Leu Leu Thr Ile Asp Glu Asp Thr Thr Ile Lys Gln Phe Lys Lys
                485                 490                 495

Glu Leu Asn Trp Asn Ala Ala Tyr Tyr Lys Leu Ala Gly Gly Leu
            500                 505                 510

<210> SEQ ID NO 31
<211> LENGTH: 27
<212> TYPE: DNA
<213> ORGANISM: Artificial
<220> FEATURE:

<223> OTHER INFORMATION: primer DPF

<400> SEQUENCE: 31
aaaccggttt cttcttcaga ttccctc    27

<210> SEQ ID NO 32
<211> LENGTH: 36
<212> TYPE: DNA
<213> ORGANISM: Artificial
<220> FEATURE:
<223> OTHER INFORMATION: primer DPR

<400> SEQUENCE: 32
ttagatctct agatttatgt atgtgttttt tgtagt    36

<210> SEQ ID NO 33
<211> LENGTH: 30
<212> TYPE: DNA
<213> ORGANISM: Artificial
<220> FEATURE:
<223> OTHER INFORMATION: primer DTF

<400> SEQUENCE: 33
aagaattcgg atcccctttt cctttgtcga    30

<210> SEQ ID NO 34
<211> LENGTH: 29
<212> TYPE: DNA
<213> ORGANISM: Artificial
<220> FEATURE:
<223> OTHER INFORMATION: primer DTR

<400> SEQUENCE: 34
aactcgagcc taggaagcct tcgagcgtc    29

<210> SEQ ID NO 35
<211> LENGTH: 436
<212> TYPE: PRT
<213> ORGANISM: Fusobacterium mortiferum

<400> SEQUENCE: 35

```
Met Glu Phe Phe Lys Gly Ile Asp Lys Val Lys Tyr Glu Gly Val Lys
1               5                   10                  15

Thr Asn Asn Leu Leu Ala Phe Ala His Tyr Asn Pro Glu Glu Val Ile
            20                  25                  30

Leu Gly Lys Lys Met Lys Asp His Leu Lys Phe Ala Met Ser Tyr Trp
        35                  40                  45

His Thr Leu Thr Gly Glu Gly Thr Asp Pro Phe Gly Asn Ala Thr Met
    50                  55                  60

Asp Arg Glu Trp Asn Glu Tyr Thr Pro Met Glu Lys Ala Lys Ala Arg
65                  70                  75                  80

Val Lys Ala Gly Phe Glu Phe Met Glu Lys Leu Gly Leu Glu Tyr Phe
                85                  90                  95

Cys Phe His Asp Lys Asp Ile Ala Pro Glu Ala Glu Thr Leu Glu Glu
            100                 105                 110

Tyr His Arg Asn Leu Asp Glu Ile Val Asp Leu Ile Glu Glu Met
            115                 120                 125

Lys Arg Thr Gly Ile Lys Leu Leu Trp Gly Thr Ser Asn Met Phe Ser
    130                 135                 140

His Pro Arg Phe Met His Gly Ala Ala Thr Ser Cys Asn Ala Asp Val
145                 150                 155                 160
```

Phe Ala Tyr Ala Ala Ala Gln Thr Lys Lys Ala Leu Glu Ile Thr Lys
                165                 170                 175

Arg Leu Asn Gly Thr Gly Tyr Val Phe Trp Gly Gly Arg Glu Gly Tyr
            180                 185                 190

Glu Thr Leu Leu Asn Thr Asp Ile Gly Leu Glu Leu Asp Asn Leu Ala
        195                 200                 205

Arg Phe Leu Gln Met Ala Val Asp Tyr Ala Lys Lys Ile Gly Phe Glu
    210                 215                 220

Gly Gln Phe Phe Ile Glu Pro Lys Pro Lys Glu Pro Thr Lys His Gln
225                 230                 235                 240

Tyr Asp Phe Asp Thr Thr Thr Val Leu Glu Phe Leu Arg Lys Tyr Asn
                245                 250                 255

Leu Asp Lys Tyr Phe Lys Met Asn Ile Glu Ala Asn His Ala Thr Leu
            260                 265                 270

Ala Gly His Thr Phe Gln His Glu Leu Cys Thr Ala Arg Ile Asn Gly
        275                 280                 285

Val Phe Gly Ser Ile Asp Ala Asn Gln Gly Asp Met Leu Leu Gly Trp
    290                 295                 300

Asp Thr Asp Gln Phe Pro Thr Asn Val Tyr Asp Ala Val Leu Ala Met
305                 310                 315                 320

Tyr Glu Thr Leu Leu Ala Gly Gly Phe Lys Glu Gly Gly Leu Asn Phe
                325                 330                 335

Asp Ala Lys Val Arg Arg Gly Ser Phe Glu Pro Lys Asp Leu Phe Tyr
            340                 345                 350

Ala Tyr Ile Ser Gly Met Asp Thr Phe Ala Lys Gly Leu Lys Val Ala
        355                 360                 365

Ala Lys Leu Ile Glu Asp Gly Thr Phe Glu Lys Ile Lys Val Glu Arg
    370                 375                 380

Tyr Ser Ser Tyr Thr Thr Gly Ile Gly Lys Gln Ile Val Asn Gly Glu
385                 390                 395                 400

Val Gly Phe Glu Glu Leu Ser Lys Tyr Ala Leu Thr Asn Gly Val Lys
                405                 410                 415

Lys Asn Ser Ser Gly Arg Gln Glu Met Leu Glu Asn Ile Leu Asn Arg
            420                 425                 430

Tyr Ile Tyr Glu
        435

<210> SEQ ID NO 36
<211> LENGTH: 438
<212> TYPE: PRT
<213> ORGANISM: Clostridium phytofermentans

<400> SEQUENCE: 36

Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu

```
                85                  90                  95
Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
            115                 120                 125

Lys Met Asp Gln Thr Gly Ile Lys Leu Leu Trp Gly Thr Ala Asn Asn
            130                 135                 140

Phe Ser His Pro Arg Phe Met His Gly Ala Ser Thr Ser Cys Asn Ala
145                 150                 155                 160

Asp Val Phe Ala Tyr Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
                195                 200                 205

Met Ala Arg Leu Met Lys Met Ala Val Glu Tyr Gly Arg Ala Asn Gly
            210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
            275                 280                 285

Asn Gly Ala Phe Gly Ser Val Asp Ala Asn Gln Gly Asp Pro Asn Leu
            290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
            325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
            355                 360                 365

Lys Ala Ala Glu Ile Ile Asp Asp Gly Arg Ile Ala Lys Phe Val Asp
            370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Glu Thr Ile Val
            420                 425                 430

Asn Asn Ile Leu Phe Arg
            435

<210> SEQ ID NO 37
<211> LENGTH: 438
<212> TYPE: PRT
<213> ORGANISM: Bacteroides uniformis

<400> SEQUENCE: 37

Met Ala Thr Lys Glu Tyr Phe Pro Gly Ile Gly Lys Ile Lys Phe Glu
1               5                   10                  15
```

```
Gly Lys Glu Ser Lys Asn Pro Met Ala Phe Arg Tyr Tyr Asp Ala Asp
             20                  25                  30

Lys Val Ile Met Gly Lys Met Ser Glu Trp Leu Lys Phe Ala Met
         35                  40                  45

Ala Trp Trp His Thr Leu Cys Ala Glu Gly Gly Asp Gln Phe Gly Gly
 50                  55                  60

Gly Thr Lys Lys Phe Pro Trp Asn Gly Glu Ala Asp Lys Val Gln Ala
 65                  70                  75                  80

Ala Lys Asn Lys Met Asp Ala Gly Phe Glu Phe Met Gln Lys Met Gly
                 85                  90                  95

Ile Glu Tyr Tyr Cys Phe His Asp Val Asp Leu Cys Glu Glu Ala Glu
            100                 105                 110

Thr Ile Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Ile Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Gly Gly Phe Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Glu Ser Pro Tyr Lys Lys Met
370                 375                 380

Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Val Ala Tyr Ala Lys Ala
                405                 410                 415

Asn Gly Glu Pro Lys Gln Thr Ser Gly Lys Gln Glu Leu Tyr Glu Ala
            420                 425                 430

Ile Val Asn Met Tyr Cys
```

<210> SEQ ID NO 38
<211> LENGTH: 1311
<212> TYPE: DNA
<213> ORGANISM: Fusobacterium mortiferum

<400> SEQUENCE: 38

| | | | | | |
|---|---|---|---|---|---|
| atggaattct | tcaagggtat | cgacaaggtt | aagtacgaag | gtgttaagac | caacaacttg | 60 |
| ttggctttcg | ctcactacaa | cccagaagaa | gttatcttgg | gtaagaagat | gaaggaccac | 120 |
| ttgaagttcg | ctatgtctta | ctggcacacc | ttgaccggtg | aaggtaccga | cccattcggt | 180 |
| aacgctacca | tggacagaga | atggaacgaa | tacacccca | tggaaaaggc | taaggctaga | 240 |
| gttaaggctg | gtttcgaatt | catggaaaag | ttgggtttgg | aatacttctg | tttccacgac | 300 |
| aaggacatcg | ctccagaagc | tgaaaccttg | gaagaatacc | acagaaactt | ggacgaaatc | 360 |
| gttgacttga | tcgaagaaga | aatgaagaga | accggtatca | agttgttgtg | gggtacctct | 420 |
| aacatgttct | ctcacccaag | attcatgcac | ggtgctgcta | cctcttgtaa | cgctgacgtt | 480 |
| ttcgcttacg | ctgctgctca | aaccaagaag | gctttggaaa | tcaccaagag | attgaacggt | 540 |
| accggttacg | ttttctgggg | tggtagagaa | ggttacgaaa | ctttgttgaa | caccgacatc | 600 |
| ggtttggaat | ggacaacttt | ggctagattc | ttgcaaatgg | ctgttgacta | cgctaagaag | 660 |
| atcggtttcg | aaggtcaatt | cttcatcgaa | ccaaagccaa | aggaaccaac | caagcaccaa | 720 |
| tacgacttcg | acaccaccac | cgttttggaa | ttcttgagaa | agtacaactt | ggacaagtac | 780 |
| ttcaagatga | acatcgaagc | taaccacgct | accttggctg | tcacaccttc | caacacgaa | 840 |
| ttgtgtaccg | ctagaatcaa | cggtgttttc | ggttctatcg | acgctaacca | aggtgacatg | 900 |
| ttgttgggtt | gggacaccga | ccaattccca | accaacgttt | acgacgctgt | tttggctatg | 960 |
| tacgaaacat | tgttggctgg | tggtttcaag | gaaggtggtt | tgaacttcga | cgctaaggtt | 1020 |
| agaagaggtt | ctttcgaacc | aaaggacttg | ttctacgctt | acatctctgg | tatggacacc | 1080 |
| ttcgctaagg | gtttgaaggt | tgctgctaag | ttgatcgaag | acggtacctt | cgaaaagatc | 1140 |
| aaggttgaaa | gatactcttc | ttacaccacc | ggtatcggta | agcaaatcgt | taacggtgaa | 1200 |
| gttggtttcg | aagaattgtc | taagtacgct | ttgaccaacg | gtgttaagaa | gaactcttct | 1260 |
| ggtagacaag | aaatgttgga | aaacatcttg | aacagataca | tctacgaata | g | 1311 |

<210> SEQ ID NO 39
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is either Gly or Pro.
<220> FEATURE:
<221> NAME/KEY: misc_feature
<222> LOCATION: (9)..(9)
<223> OTHER INFORMATION: Xaa is either Tyr, Ser, Thr or Ala.

<400> SEQUENCE: 39

Val Xaa Trp Xaa Gly Arg Glu Gly Xaa
1               5

```
<210> SEQ ID NO 40
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is Leu, Ile, Val or Met.
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is Glu or Gln.

<400> SEQUENCE: 40

Xaa Glu Pro Lys Pro Xaa Xaa Pro
1               5
```

XYLOSE ISOMERASE GENES AND THEIR USE IN FERMENTATION OF PENTOSE SUGARS

CROSS REFERENCE TO RELATED APPLICATIONS

This application is a divisional of U.S. patent application Ser. No. 13/142,124, filed Sep. 13, 2011 (now U.S. Pat. No. 9,334,488), which claims priority from National Stage Entry of PCT/NL2009/050803, filed Dec. 24, 2009, and U.S. Provisional Patent Application No. 61/140,795, filed Dec. 24, 2008, the contents of which are incorporated herein by reference in their entireties.

FIELD OF THE INVENTION

The present invention relates to the use of nucleic acid sequences encoding xylose isomerases in the transformation of a eukaryotic microbial host cell to confer to the host cell the ability of isomerising xylose to xylulose. The transformed host cell is used in a process for the production of ethanol and other fermentation products by fermentation of a pentose-containing medium.

BACKGROUND OF THE INVENTION

Economically viable ethanol production from the hemicellulose fraction of plant biomass requires the simultaneous conversion of both pentoses and hexoses at comparable rates and with high yields. Yeasts, in particular *Saccharomyces* spp., are the most appropriate candidates for this process since they can grow fast on hexoses, both aerobically and anaerobically. Furthermore, they are much more resistant to the toxic environment of lignocellulose hydrolysates than (genetically modified) bacteria.

Although wild-type *S. cerevisiae* strains can slowly metabolise the pentose sugar xylulose, they are not capable of metabolising xylose. Already in the 1980's it was suggested that metabolic engineering of yeasts for xylose utilization should be based on the introduction of xylose isomerase (XI, EC 5.3.1.5) rather than expressing heterologous xylose reductase and xylitol dehydrogenase to convert xylose into xylulose. Unfortunately, all attempts of introducing a bacterial xylose isomerase in *S. cerevisiae* have failed to produce a functionally expressed xylose isomerase with the notable exception of the *T. thermophilus* isomerase. This enzyme was functionally expressed in *S. cerevisiae* but only very low activities were observed at growth permitting temperatures. This situation drastically changed when a newly discovered xylose isomerase from the anaerobic fungus *Piromyces* Sp.E2 was introduced in *S. cerevisiae* and high levels of enzyme activities were observed enabling this strain to grow anaerobically and produce ethanol from xylose (WO 03/062430 and WO 06/009434). Such yeast strains for the first time provided specific rates of xylose consumption and ethanol formation that are compatible with ethanol production at a commercial scale.

Since the discovery of the functional expression of the *Piromyces* xylose isomerase in yeast several reports have appeared of functional expression in yeasts of other xylose isomerases, all of which share more than 70% amino acid sequence identity with the *Piromyces* enzyme, such e.g. the bacterial xylose isomerase from *Bacteroides* (WO 04/099381; WO 06/009434; WO 09/109633), and the fungal xylose isomerases from *Cyllamyces* (WO 04/099381) and *Orpinomyces* (Madhavan et al., 2008, DOI 10.1007/s00253-008-1794-6).

However, prior to Dec. 24, 2008 no reports have issued of functional expression in yeasts of xylose isomerases having less than 70% amino acid sequence identity with the *Piromyces* enzyme. More recently, in February 2009, Brat et al. (2009, Appl. Environ. Microbiol. 75: 2304-2311) published functional expression in the yeast *S. cerevisiae* of a xylose isomerise from the anaerobic bacterium *Clostridium phytofermentans*, the amino acid sequence of which shares only 52% identity with that of the *Piromyces* enzyme.

To date some 450 xylose isomerase amino acid sequences are publicly available in Genbank and other sequence databases, including the xylose isomerase sequences of *Piromyces, Cyllamyces aberensis, Physcomitrella patens, Arabidopsis thaliana, Haemophilus somnus, Ciona intestinalis, Clostridium difficile, Thermatoga maritime, Bacteroides fragilis, Burkholderia phytofirmans, Arthrobacter aurescens* and *Fusobacterium mortiferum*.

There is, however, still a need in the art for nucleotide sequences encoding other xylose isomerases that may be used to transform host cells like *S. cerevisiae* to confer to them the ability of isomerising xylose to xylulose, so as to enable the use of thus transformed host cell in processes for the production of ethanol or other fermentation products by fermentation of pentose-containing feedstock.

DESCRIPTION OF THE INVENTION

Definitions

The enzyme "xylose isomerase" (EC 5.3.1.5) is herein defined as an enzyme that catalyses the direct isomerisation of D-xylose into D-xylulose and vice versa. The enzyme is also known as a D-xylose ketoisomerase. Some xylose isomerases are also capable of catalysing the conversion between D-glucose and D-fructose and are therefore sometimes referred to as glucose isomerase. Xylose isomerases require magnesium as cofactor. Xylose isomerases of the invention may be further defined by their amino acid sequence as herein described below. Likewise xylose isomerases may be defined by the nucleotide sequences encoding the enzyme as well as by nucleotide sequences hybridising to a reference nucleotide sequence encoding a xylose isomerase as herein described below. A unit (U) of xylose isomerase activity is herein defined as the amount of enzyme producing 1 nmol of xylulose per minute, in a reaction mixture containing 50 mM phosphate buffer (pH 7.0), 10 mM xylose and 10 mM $MgCl_2$, at 37° C. Xylulose formed was determined by the method of Dische and Borenfreund (1951, J. Biol. Chem. 192: 583-587) or by HPLC as described in the Examples.

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention is ClustalW (1.83) using a blosum matrix and default settings (Gap opening penalty: 10; Gap extension penalty: 0.05). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1):387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to tip or phe; and, Val to ile or leu.

Nucleotide sequences encoding xylose isomerases of the invention may also be defined by their capability to hybridise with the nucleotide sequences of SEQ ID NO. 2, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleotide sequences that are capable of affecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

"Fungi" (singular fungus) are herein understood as heterotrophic eukaryotic microorganism that digest their food externally, absorbing nutrient molecules into their cells. Fungi are a separate kingdom of eukaryotic organisms and include yeasts, molds, and mushrooms. The terms fungi, fungus and fungal as used herein thus expressly includes yeasts as well as filamentous fungi.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'nontranslated sequence (3'end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

DETAILED DESCRIPTION OF THE INVENTION

To date some 450 xylose isomerase amino acid sequences are publicly available in Genbank and other sequence databases. Among them are a number of amino acid sequences of xylose isomerases that are known for the ability of functional expression in yeasts, including e.g. xylose isomerases from anaerobic fungi such *Piromyces, Cyllamyces,* and *Orpinomyces,* as well as bacterial xylose isomerases from *Bacteroides,* all of which share more than 70% amino acid sequence identity with the *Piromyces* enzyme. The present inventors have now surprisingly found amino acid sequences of xylose isomerases that are not related to the *Piromyces* enzyme in the sense that they share less than 70% amino acid sequence identity with the amino acid sequence of *Piromyces* enzyme, and that nonetheless have the ability of functional (i.e. active) expression in yeasts. Furthermore, the present inventors have identified a number of amino acid sequence elements that are shared among all xylose isomerases with the ability of functional expression in yeasts. Functional expression of a xylose isomerase in a yeast is herein understood as expression of a codon-optimised coding sequence for a xylose isomerase from a glycolytic promoter on a 2μ-based plasmid in *S. cerevisiae* that allows the detectable growth of the yeast on xylose as sole carbon source, preferably under anaerobic conditions with production of ethanol at the expense of xylose, more preferably with at least one of a growth rate, biomass and ethanol yield that is at least 10, 20, 50 or 80% of that achieved with a codon-optimised *Piromyces* xylose isomerase coding sequence under otherwise identical conditions. Preferably functional expression is expression that allows the detectable growth of the yeast on xylose as sole carbon source at a temperature which is lower than 35, 33, 30 or 28° C. and at a temperature which is higher than 20, 22, or 25° C.

In a first aspect the present invention relates to a transformed host cell that has the ability of isomerising xylose to xylulose. The ability of isomerising xylose to xylulose is conferred to the host cell by transformation of the host cell with a nucleic acid construct comprising a nucleotide sequence encoding a xylose isomerase. The transformed host cell's ability to isomerise xylose into xylulose is understood to mean the direct isomerisation of xylose, in a single reaction catalysed by a xylose isomerase, to xylulose, as opposed to the two step conversion of xylose into xylulose via a xylitol intermediate as catalysed by xylose reductase and xylitol dehydrogenase, respectively.

In one embodiment the nucleotide sequence encoding the xylose isomerase is selected from the group consisting of:
(a) a nucleotide sequence encoding a polypeptide with xylose isomerase activity, which polypeptide comprises an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 1 (*C. difficile*);
(b) a nucleotide sequence encoding a polypeptide with xylose isomerase activity, which polypeptide comprises an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 2 (*Ciona*);
(c) a nucleotide sequence encoding a polypeptide with xylose isomerase activity, which polypeptide comprises an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 35 (*F. mortiferum*);
(d) a nucleotide sequence the complementary strand of which hybridises to a nucleotide sequence of (a), (b) or (c); and,
(e) a nucleotide sequence the sequence of which differs from the sequence of a nucleotide sequence of (d) due to the degeneracy of the genetic code.

In one embodiment the nucleotide sequence encoding the xylose isomerase encodes an amino acid sequence comprising one or amino acid sequence elements that are shared among xylose isomerases with the ability of functional expression in yeasts. In this embodiment the nucleotide sequence encoding the xylose isomerase encodes an amino acid sequence comprising one or amino acid sequence elements selected from the group consisting of:
(a) a methionine residue at position 91;
(b) the amino acid sequence TGIKLL at positions 134-139;
(c) a phenylalanine residue at position 230;
(d) the amino acids phenylalanine and lysine at positions 264 and 265, respectively;
(e) the amino acid sequence TLAGH at positions 274-278;
(f) the amino acid sequence RYASF at positions 387-391;
(g) a glycine residue at position 394; and,
(h) an alanine residue at position 431.

In this embodiment the encoded xylose isomerase may comprise at least 1, 2, 3, 4, 5, 6, 7 or all 8 of the elements (a)-(h) in all possible combinations. Thus, in this embodiment the encoded xylose isomerase may comprise the following element or combinations of elements: (a); (b); (c); (d); (e); (f); (g); (h); (a) and (b); (a) and (c); (a) and (d); (a) and (e); (a) and (f); (a) and (g); (a) and (h); (b) and (c); (b) and (d); (b) and (e); (b) and (f); (b) and (g); (b) and (h); (c) and (d); (c) and (e); (c) and (f); (c) and (g); (c) and (h); (d) and (e); (d) and (f); (d) and (g); (d) and (h); (e) and (f); (e) and (g); (e) and (h); (f) and (g); (f) and (h); (g) and (h); (a), (b) and (c); (a), (b) and (d); (a), (b) and (e); (a), (b) and (f); (a), (b) and (g); (a), (b) and (h); (a), (c) and (d); (a), (c) and (e); (a), (c) and (f); (a), (c) and (g); (a), (c) and (h); (a), (d) and (e); (a), (d) and (f); (a), (d) and (g); (a), (d) and (h); (a), (e) and (f); (a), (e) and (g); (a), (e) and (h); (a), (f) and (g); (a), (f) and (h); (a), (g) and (h); (b), (c) and (d); (b), (c) and (e); (b), (c) and (f); (b), (c) and (g); (b), (c) and (h); (b), (d) and (e); (b), (d) and (f); (b), (d) and (g); (b), (d) and (h); (b), (e) and (f); (b), (e) and (g); (b), (e) and (h); (b), (f) and (g); (b), (f) and (h); (b), (g) and (h); (c), (d) and (e); (c), (d) and (f); (c), (d) and (g); (c), (d) and (h); (c), (e) and (f); (c), (e) and (g); (c), (e) and (h); (c), (f) and (g); (c), (f) and (h); (c), (g) and (h); (d), (e) and (f); (d), (e) and (g); (d), (e) and (h); (d), (f) and (g); (d), (f) and (h); (d), (g) and (h); (e), (f) and (g); (e), (f) and (h); (e), (g) and (h); (f), (g) and (h); (a), (b), (c) and (d); (a), (b), (c) and (e); (a), (b), (c) and (f); (a), (b), (c) and (g); (a), (b), (c) and (h); (a), (b), (d) and (e); (a), (b), (d) and (f); (a), (b), (d) and (g); (a), (b), (d) and (h); (a), (b), (e) and (f); (a), (b), (e) and (g); (a), (b), (e) and (h); (a), (b), (f) and (g); (a), (b), (f) and (h); (a), (b), (g) and (h); (a), (c), (d) and (e); (a), (c), (d) and (f); (a), (c), (d) and (g); (a), (c), (d) and (h); (a), (c), (e) and (f); (a), (c), (e) and (g); (a), (c), (e) and (h); (a), (c), (f) and (g); (a), (c), (f) and (h); (a), (c), (g) and (h); (a), (d), (e) and (f); (a), (d), (e) and (g); (a), (d), (e) and (h); (a), (d), (f) and (g); (a), (d), (f) and (h); (a), (d), (g) and (h); (a), (e), (f) and (g); (a), (e), (f) and (h); (a), (e), (g) and (h); (a), (f), (g) and (h); (b), (c), (d) and (e); (b), (c), (d) and (f); (b), (c), (d) and (g); (b), (c), (d) and (h); (b), (c), (e) and (f); (b), (c), (e) and (g); (b), (c), (e) and (h); (b), (c), (f) and (g); (b), (c), (f) and (h); (b), (c), (g) and (h); (b), (d), (e) and (f); (b), (d), (e) and (g); (b), (d), (e) and (h); (b), (d), (f) and (g); (b), (d), (f) and (h); (b), (d), (g) and (h); (b), (e), (f) and (g); (b), (e), (f) and (h); (b), (e), (g) and (h); (b), (f), (g) and (h); (c), (d), (e) and (f); (c), (d), (e) and (g); (c), (d), (e) and (h); (c), (d), (f) and (g); (c), (d), (f) and (h); (c), (d), (g) and (h); (c), (e), (f) and (g); (c), (e), (f) and (h); (c), (e), (g) and (h); (c), (f), (g) and (h); (d), (e), (f) and (g); (d), (e), (f) and (h); (d), (e), (g) and (h); (d), (f), (g) and (h); (e), (f), (g) and (h); (a), (b), (c), (d) and (e); (a), (b), (c), (d) and (f); (a), (b), (c), (d) and (g); (a), (b), (c), (d) and (h); (a), (b), (c), (e) and (f); (a), (b), (c), (e) and (g); (a), (b), (c), (e) and (h); (a), (b), (c), (f) and (g); (a), (b), (c), (f) and (h); (a), (b), (c), (g) and (h); (a), (b), (d), (e) and (f); (a), (b), (d), (e) and (g); (a), (b), (d), (e) and (h); (a), (b), (d), (f) and (g); (a), (b), (d), (f) and (h); (a), (b), (d), (g) and (h); (a), (b), (e), (f) and (g); (a), (b), (e), (f) and (h); (a), (b), (e), (g) and (h); (a), (b), (f), (g) and (h); (a), (c), (d), (e) and (f); (a), (c), (d), (e) and (g); (a), (c), (d), (e) and (h); (a), (c), (d), (f) and (g); (a), (c), (d), (f) and (h); (a), (c), (d), (g) and (h); (a), (c), (e), (f) and (g); (a), (c), (e), (f) and (h); (a), (c), (e), (g) and (h); (a), (c), (f), (g) and (h); (a), (d), (e), (f) and (g); (a), (d), (e), (f) and (h); (a), (d), (e), (g) and (h); (a), (d), (f), (g) and (h); (a), (e), (f), (g) and (h); (b), (c), (d), (e) and (f); (b), (c), (d), (e) and (g); (b), (c), (d), (e) and (h); (b), (c), (d), (f) and (g); (b), (c), (d), (f) and (h); (b), (c), (d), (g) and (h); (b), (c), (e), (f) and (g); (b), (c), (e), (f) and (h); (b), (c), (e), (g) and (h); (b), (c), (f), (g) and (h); (b), (d), (e), (f) and (g); (b), (d), (e), (f) and (h); (b), (d), (e), (g) and (h); (b), (d), (f), (g) and (h); (b), (e), (f), (g) and (h); (c), (d), (e), (f) and (g); (c), (d), (e), (f) and (h); (c), (d), (e), (g) and (h); (c), (d), (f), (g) and (h); (c), (e), (f), (g) and (h); (d), (e), (f), (g) and (h); (a), (b), (c), (d), (e) and (f); (a), (b), (c), (d), (e) and (g); (a), (b), (c), (d), (e) and (h); (a), (b), (c), (d), (f) and (g); (a), (b), (c), (d), (f) and (h); (a), (b), (c), (d), (g) and (h); (a), (b), (c), (e), (f) and (g); (a), (b), (c), (e), (f) and (h); (a), (b), (c), (e), (g) and (h); (a), (b), (c), (f), (g) and (h); (a), (b), (d), (e), (f) and (g); (a), (b), (d), (e), (f) and (h); (a), (b), (d), (e), (g) and (h); (a), (b), (d), (f), (g) and (h); (a), (b), (e), (f), (g) and (h); (a), (c), (d), (e), (f) and (g); (a), (c), (d), (e), (f) and (h); (a), (c), (d), (e), (g) and (h); (a), (c), (d), (f), (g) and (h); (a), (c), (e), (f), (g) and (h); (a), (d), (e), (f), (g) and (h); (b), (c), (d), (e), (f) and (g); (b), (c), (d), (e), (f) and (h); (b), (c), (d), (e), (g) and (h); (b), (c), (d), (f), (g) and (h); (b), (c), (e), (f), (g) and (h); (b), (d), (e), (f), (g) and (h); (c), (d), (e), (f), (g) and (h); (a), (b), (c), (d), (e), (f) and (g); (a), (b), (c), (d), (e), (f) and (h); (a), (b), (c), (d), (e), (g) and (h); (a), (b), (c), (d), (f), (g) and (h); (a), (b), (c), (e), (f), (g) and (h); (a), (b), (d), (e), (f), (g) and (h); (a), (c), (d), (e), (f), (g) and (h); and finally, (b), (c), (d), (e), (f), (g) and (h). Furthermore, amino acid sequences in positions corresponding to those of amino acid sequences in (b), (d), (e) and (f) may differ preferably in no more than 1, 2, or 3 amino acid from the amino acid sequences in (b), (d), (e) and (f). Preferably, element (b) at least consists of I at position 136; element (d) at least consists of F at position 264; element (f) at least consists of an F or a Y at position 391. In one preferred embodiment, the encoded xylose isomerase comprises at least one of elements (a), (f), (g) and (h), More preferably, the encoded xylose isomerase in addition comprises at least one of elements (b) and (c) and most preferably the encoded xylose isomerase in addition comprises at least one of elements (d) and (e). In one preferred embodiment, the encoded xylose isomerase comprises at least element (a), more preferably in addition the isomerise comprises at least elements (b), (c) and/or (g), still more preferably in addition the isomerise comprises at least elements (d), (f) and/or (h), most preferably the isomerise additionally comprises element (e).

Amino acid positions of the above sequence elements (a)-(h) refer to positions in the reference amino acid sequence of the *Piromyces* xylose isomerase of SEQ ID NO: 3. In amino acid sequences of the invention other than SEQ ID NO: 3, preferably, the amino acid positions of sequence elements (a)-(h) are present in amino acid positions corresponding to the positions of sequence elements (a)-(h) in SEQ ID NO: 3, preferably in a ClustalW (1.83) sequence alignment using default settings. The skilled person will know how to identify corresponding amino acid positions in xylose isomerase amino acid sequences other than SEQ ID NO: 3 using amino acid sequence alignment algorithms as defined hereinabove. An example of such an alignment is depicted in Table 4, which shows a Clustal W (1.83) multiple sequence alignment of xylose isomerase amino acid sequences from organisms indicated on the left. The shaded amino acids the *Piromyces* sequence (SEQ ID NO: 3) in Table 4 indicate sequence elements that are shared among xylose isomerases that have the ability of functional expression in yeast.

In one embodiment the nucleotide sequence encoding the xylose isomerase encodes an amino acid sequence that is not one or more of SEQ ID NO: 3-7. Preferably the nucleotide sequence encoding the xylose isomerase does not have an amino acid sequence that has more than (or has an amino acid sequence that has less than) 99, 98, 97, 96, 95, 94, 93, 92, 91, 90, 89, 88, 87, 86, 85, 84, 83, 82, 81, 80, 79, 78, 77, 76, 75, 74, 73, 72, 71 or 70% sequence identity with at least one amino acid sequence selected from the group consisting of SEQ ID NO: 3-7.

In one embodiment the nucleotide sequence encoding the xylose isomerase encodes an amino acid sequence that is not one or more of SEQ ID NO: 35. Preferably the nucleotide sequence encoding the xylose isomerase does not have an amino acid sequence that has more than (or has an amino acid sequence that has less than) 99, 98, 97, 96, 95, 94, 93, 92, 91, 90, 89, 88, 87, 86, 85, 84, 83, 82, 81, 80, 79, 78, 77, 76, 75, 74, 73, 72, 71 or 70% sequence identity with at least one amino acid sequence selected from the group consisting of SEQ ID NO: 35.

In one embodiment the nucleotide sequence encoding the xylose isomerase encodes an amino acid sequence that is not an amino acid sequences selected from the group consisting of:
(a) the *Piromyces* xylose isomerase disclosed in WO 03/062340;
(b) the *Bacteroides thetaiotaomicron* xylose isomerases disclosed in WO 04/099381 and in WO 06/009434);
(c) the *Cyllamyces* xylose isomerase disclosed in WO 04/099381; and,
(d) the *Orpinomyces* xylose isomerase disclosed in Madhavan et al. (2008, supra).

Preferably the nucleotide sequence encoding the xylose isomerase does not have an amino acid sequence that has more than (or has an amino acid sequence that has less than) 99, 98, 97, 96, 95, 94, 93, 92, 91, 90, 89, 88, 87, 86, 85, 84, 83, 82, 81, 80, 79, 78, 77, 76, 75, 74, 73, 72, 71 or 70% sequence identity with at least one amino acid sequence selected from the group consisting of:
(a) the *Piromyces* xylose isomerase disclosed in WO 03/062340;
(b) the *Bacteroides thetaiotaomicron* xylose isomerases disclosed in WO 04/099381 and in WO 06/009434);
(c) the *Cyllamyces* xylose isomerase disclosed in WO 04/099381; and,
(d) the *Orpinomyces* xylose isomerase disclosed in Madhavan et al. (2008, supra).

In one embodiment the nucleotide sequence encoding the xylose isomerase encodes an amino acid sequence that is not an amino acid of a xylose isomerase from an anaerobic fungus of the Family Neocallimastigaceae, such as a fungus from a genus selected from the group consisting of: *Anaeromyces, Caecomyces, Cyllamyces, Neocallimastix, Orpinomyces, Piromyces*, and *Ruminomyces*.

In one embodiment the nucleotide sequence encoding the xylose isomerase encodes an amino acid sequence that is not an amino acid of a xylose isomerase from a bacterium from the genus *Bacteroides* or *Parabacteroides*.

The nucleotide sequences of the invention encode a novel class of xylose isomerases that may be functionally expressed in eukaryotic microbial host cells of the invention as defined below. The nucleotide sequences of the invention preferably encode xylose isomerases that naturally occurs in certain fungi, bacteria and tunicate.

A preferred nucleotide sequence of the invention thus encodes a xylose isomerase with an amino acid sequence that is identical to that of a xylose isomerase that is obtainable from (or naturally occurs in) a bacterium of the Family Clostridiaceae, more preferably a bacterium of the genus *Clostridium*, of which *C. difficile* is most preferred.

A preferred nucleotide sequence of the invention thus encodes a xylose isomerase with an amino acid sequence that is identical to that of a xylose isomerase that is obtainable from (or naturally occurs in) a bacterium of the Family Fusobacteriaceae, more preferably a bacterium of the genus *Fusobacterium*, of which *F. mortiferum* is most preferred.

A preferred nucleotide sequence of the invention thus encodes a xylose isomerase with an amino acid sequence that is identical to that of a xylose isomerase that is obtainable from (or naturally occurs in) a tunicate, preferably a tunicate of the Family Cionidae, more preferably a tunicate of the genus *Ciona*, of which *C. intestinales* is most preferred.

In another embodiment the nucleotide sequence encoding the xylose isomerase is selected from the group consisting of:
  (a) a nucleotide sequence encoding a polypeptide with xylose isomerase activity, which polypeptide comprises an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of at least one of SEQ ID NO. 8, 9, 11 or 13;
  (b) a nucleotide sequence the complementary strand of which hybridises to a nucleotide sequence of (a) or (b); and,
  (c) a nucleotide sequence the sequence of which differs from the sequence of a nucleotide sequence of (d) due to the degeneracy of the genetic code.

It is however understood that nucleotide sequences encoding engineered forms of any of the xylose isomerases defined above and that comprise one or more amino acid substitutions, insertions and/or deletions as compared to the corresponding naturally occurring xylose isomerases but that are within the ranges of identity or similarity as defined herein are expressly included in the invention. Therefore, in one embodiment the nucleotide sequence of the invention encodes a xylose isomerase amino acid sequence comprising a xylose isomerase signature sequence as defined by Meaden et al. (1994, *Gene*, 141: 97-101): VXW{GP}GREG{YSTA} (SEQ ID NO:39) (corresponding to positions 187-195 of SEQ ID NO:3) and {LIVM}EPKPX{EQ}P (SEQ ID N0:40) (corresponding to positions 232-239 of SEQ ID NO:3), wherein "X" can be any amino acid and wherein one of the amino acids in braces can be present at that position in the signature sequence. A xylose isomerase amino acid sequence of the invention further preferably comprises the conserved amino acid residues His-102, Asp-105, and Asp-340, which constitute a triad directly involved in catalysis, Lys-235 plays a structural as well as a functional catalytic role, and Glu-233, which is involved in binding of the magnesium (Vangrysperre et al., 1990, *Biochem. J.* 265: 699-705; Henrick et al., *J. Mol. Biol.* 208: 129-157; Bhosale et al., 1996 *Microbiol. Rev.* 60: 280-300) Amino acid positions of the above signature sequences and conserved residues refer to positions in the reference amino acid sequence of the *Piromyces* xylose isomerase of SEQ ID NO: 3. In amino acid sequences of the invention other than SEQ ID NO: 3, preferably, the amino acid positions of the above signature sequences and conserved residues are present in amino acid positions corresponding to the positions of the signature sequences and conserved residues in SEQ ID NO: 3, preferably in a ClustalW (1.83 or 1.81) sequence alignment using default settings. The skilled person will know how to identify corresponding amino acid positions in xylose isomerase amino acid sequences other than SEQ ID NO: 3 using amino acid sequence alignment algorithms as defined hereinabove. An example of such an alignment is depicted in Table 4. In addition, to date some 450 amino acid sequences of xylose isomerases are known in the art and new ones are added continuously being added. Sequence alignments of SEQ ID NO: 3 and the xylose isomerase sequences of the invention with these known and new xylose isomerase amino acid sequences will indicate further conserved regions and amino acid positions, the conservation of which are important for structure and enzymatic activity. These regions and positions will tolerate no or only conservative amino acid substitutions Amino acid substitutions outside of these regions and positions are unlikely to greatly affect xylose isomerase activity.

The nucleotide sequence encodes a xylose isomerase that is preferably expressed in active form in the transformed host cell. Thus, expression of the nucleotide sequence in the host cell produces a xylose isomerase with a specific activity of at least 10 U xylose isomerase activity per mg protein at 25° C., preferably at least 20, 25, 30, 50, 100, 200 or 300 U per mg at 25° C. The specific activity of the xylose isomerase expressed in the transformed host cell is herein defined as the amount of xylose isomerase activity units per mg protein of cell free lysate of the host cell, e.g. a yeast cell free lysate. Determination of the xylose isomerase activity, amount of protein and preparation of the cell free lysate are as described in the Examples. Preferably, expression of the nucleotide sequence in the host cell produces a xylose isomerase with a $K_m$ for xylose that is less than 50, 40, 30 or 25 mM, more preferably, the $K_m$ for xylose is about 20 mM or less.

The nucleotide sequences of the invention, encoding polypeptides with xylose isomerase activity, are obtainable from genomic and/or cDNA of a fungus, yeast or bacterium that belongs to a phylum, class or genus as described above, using method for isolation of nucleotide sequences that are well known in the art per se (see e.g. Sambrook and Russell (2001) "Molecular Cloning: A Laboratory Manual ($3^{rd}$ edition), Cold Spring Harbor Laboratory, Cold Spring Harbor Laboratory Press, New York). The nucleotide sequences of the invention are e.g. obtainable in a process wherein a) degenerate PCR primers (such as those in SEQ ID NO.'s 14 and 15) are used on genomic and/or cDNA of a suitable organism (e.g. a fungus, bacterium or tunicate as indicated above) to generate a PCR fragment comprising part of the nucleotide sequences encoding the polypeptides with xylose isomerase activity; b) the PCR fragment obtained in a) is used as probe to screen a cDNA and/or genomic library of the organism; and c) producing a cDNA or genomic DNA comprising the nucleotide sequence encoding a polypeptide with xylose isomerase activity.

To increase the likelihood that the xylose isomerase is expressed at sufficient levels and in active form in the transformed host cells of the invention, the nucleotide sequence encoding these enzymes, as well as other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences as listed in SEQ ID NO's: 16, 17 and 38, which have been codon optimised for expression in *S. cerevisiae* cells.

The host cell to be transformed with a nucleic acid construct comprising a nucleotide sequence encoding a xylose isomerase of the invention preferably is a eukaryotic microbial host, more preferably a fungal host cell, such as a yeast or filamentous fungal host cell. Preferably the host cell is a cultured cell. The host cell of the invention, preferably is a host capable of active or passive pentose (xylose and preferably also arabinose) transport into the cell. The host cell preferably contains active glycolysis. The host cell may further preferably contains an endogenous pentose phosphate pathway and may contain endogenous xylulose kinase activity so that xylulose isomerised from xylose may be metabolised to pyruvate. The host further preferably contains enzymes for conversion of a pentose (preferably through pyruvate) to a desired fermentation product such as ethanol, lactic acid, 3-hydroxy-propionic acid, acrylic acid, acetic acid, succinic acid, citric acid, amino acids, 1,3-propane-diol, ethylene, glycerol, β-lactam antibiotics and cephalosporins. A particularly preferred host cell is a host cell that is naturally capable of alcoholic fermentation, preferably, anaerobic alcoholic fermentation. The host cell further preferably has a high tolerance to ethanol, a high tolerance to low pH (i.e. capable of growth at a pH lower than 5, 4, or 3) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified by genetic modification, preferably by self cloning or by the methods of the invention described below. A suitable cell is a cultured cell, a cell that may be cultured in fermentation process e.g. in submerged or solid state fermentation. Particularly suitable cells are eukaryotic microorganism like e.g. fungi, however, most suitable for use in the present inventions are yeasts or filamentous fungi.

Yeasts are herein defined as eukaryotic microorganisms and include all species of the subdivision Eumycotina (Yeasts: characteristics and identification, J. A. Barnett, R. W. Payne, D. Yarrow, 2000, 3rd ed., Cambridge University Press, Cambridge UK; and, The yeasts, a taxonomic study, C. P. Kurtzman and J. W. Fell (eds) 1998, 4th ed., Elsevier Science Publ. B.V., Amsterdam, The Netherlands) that predominantly grow in unicellular form. Yeasts may either grow by budding of a unicellular thallus or may grow by fission of the organism. Preferred yeasts as host cells belong to the genera *Saccharomyces*, *Kluyveromyces*, *Candida*, *Pichia*, *Schizosaccharomyces*, *Hansenula*, *Kloeckera*, *Schwanniomyces*, and *Yarrowia*. Preferably the yeast is capable of anaerobic fermentation, more preferably anaerobic alcoholic fermentation. Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as fungal host cells include *S. cerevisiae*, *S. exiguus*, *S. bayanus*, *K. lactis*, *K. marxianus* and *Schizosaccharomyces pombe*.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism of most filamentous fungi is obligately aerobic. Preferred filamentous fungi as host cells belong to the genera *Aspergillus*, *Trichoderma*, *Humicola*, *Acremonium*, *Fusarium*, and *Penicillium*.

In a transformed host cell of the invention, the nucleotide sequence encoding the xylose isomerase as defined above is preferably operably linked to a promoter that causes sufficient expression of the nucleotide sequences in the cell to confer to the cell the ability to convert xylose into xylulose. More preferably the promoter causes sufficient expression of the nucleotide sequences to confer to the cell the ability to grow on xylose as sole carbon and/or energy source, most preferably under anaerobic conditions. Suitable promoters for expression of the nucleotide sequence as defined above include promoters that are insensitive to catabolite (glucose) repression and/or that do require xylose for induction. Promoters having these characteristics are widely available and known to the skilled person. Suitable examples of such promoters include e.g. promoters from glycolytic genes such as the phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK), glucose-6-phosphate isomerase promoter (PGI1) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), the enolase promoter (ENO), the hexose(glucose) transporter promoter (HXT7), and the cytochrome c1 promoter (CYC1). Other promoters, both constitutive and inducible, and enhancers or upstream activating sequences will be known to those of skill in the art. Preferably the promoter that is operably linked to nucleotide sequence as defined above is homologous to the host cell.

The transformed host cell of the invention further preferably comprises xylulose kinase activity so that xylulose isomerised from xylose may be metabolised to pyruvate. Preferably, the cell contains endogenous xylulose kinase activity. More preferably, a cell of the invention comprises a genetic modification that increases the specific xylulose kinase activity. Preferably the genetic modification causes overexpression of a xylulose kinase, e.g. by overexpression of a nucleotide sequence encoding a xylulose kinase. The gene encoding the xylulose kinase may be endogenous to the cell or may be a xylulose kinase that is heterologous to the cell. A nucleotide sequence that may be used for overexpression of xylulose kinase in the cells of the invention is e.g. the xylulose kinase gene from *S. cerevisiae* (XKS1) as described by Deng and Ho (1990, Appl. Biochem. Biotechnol. 24-25: 193-199). Another preferred xylulose kinase is a xylose kinase that is related to the xylulose kinase from *Piromyces* (xylB; see WO 03/0624430). This *Piromyces* xylulose kinase is actually more related to prokaryotic kinase than to all of the known eukaryotic kinases such as the yeast kinase. The eukaryotic xylulose kinases have been indicated as non-specific sugar kinases, which have a broad substrate range that includes xylulose. In contrast, the prokaryotic xylulose kinases, to which the *Piromyces* kinase is most closely related, have been indicated to be more specific kinases for xylulose, i.e. having a narrower substrate range. In the cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention further preferably comprises a genetic modification that increases the flux of the pentose phosphate pathway as described in WO 06/009434. In particular, the genetic modification causes an increased flux of the non-oxidative part pentose phosphate pathway. A genetic modification that causes an increased flux of the non-oxidative part of the pentose phosphate pathway is herein understood to mean a modification that increases the flux by at least a factor 1.1, 1.2, 1.5, 2, 5, 10 or 20 as compared to the flux in a strain which is genetically identical except for the genetic modification causing the increased flux. The flux of the non-oxidative part of the pentose phosphate pathway may be measured as described in WO 06/009434.

Genetic modifications that increase the flux of the pentose phosphate pathway may be introduced in the cells of the invention in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred cell of the invention, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate 3-epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate 3-epimerase; or at least the enzymes ribulose-5-phosphate isomerase and transketolase; or at least the enzymes ribulose-5-phosphate isomerase and transaldolase; or at least the enzymes ribulose-5-phosphate 3-epimerase and transketolase; or at least the enzymes ribulose-5-phosphate 3-epimerase and transaldolase; or at least the enzymes transketolase and transaldolase; or at least the enzymes ribulose-5-phosphate 3-epimerase, transketolase and transaldolase; or at least the enzymes ribulose-5-phosphate isomerase, transketolase and transaldolase; or at least the enzymes ribulose-5-phosphate isomerase, ribulose-5-phosphate 3-epimerase, and transaldolase; or at least the enzymes ribulose-5-phosphate isomerase, ribulose-5-phosphate 3-epimerase, and transketolase. In one embodiment of the invention each of the enzymes ribulose-5-phosphate isomerase, ribulose-5-phosphate 3-epimerase, transketolase and transaldolase are overexpressed in the cell of the invention. Preferred is a cell in which the genetic modification comprises at least overexpression of the enzyme transaldolase. More preferred is a cell in which the genetic modification comprises at least overexpression of both the enzymes transketolase and transaldolase as such a host cell is already capable of anaerobic growth on xylose. In fact, under some conditions we have found that cells overexpressing only the transketolase and the transaldolase already have the same anaerobic growth rate on xylose as do cells that overexpress all four of the enzymes, i.e. the ribulose-5-phosphate isomerase, ribulose-5-phosphate 3-epimerase, transketolase and transaldolase. Moreover, cells of the invention overexpressing both of the enzymes ribulose-5-phosphate isomerase and ribulose-5-phosphate 3-epimerase are preferred over cells overexpressing only the isomerase or only the 3-epimerase as overexpression of only one of these enzymes may produce metabolic imbalances.

There are various means available in the art for overexpression of enzymes in the cells of the invention. In particular, an enzyme may be overexpressed by increasing the copynumber of the gene coding for the enzyme in the cell, e.g. by integrating additional copies of the gene in the cell's genome, by expressing the gene from an episomal multicopy expression vector or by introducing a episomal expression vector that comprises multiple copies of the gene. The coding sequence used for overexpression of the enzymes preferably is homologous to the host cell of the invention. However, coding sequences that are heterologous to the host cell of the invention may likewise be applied.

Alternatively overexpression of enzymes in the cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the cell of the invention. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence, preferably under conditions where xylose or xylose and glucose are available as carbon sources, more preferably as major carbon sources (i.e. more than 50% of the available carbon source consists of xylose or xylose and glucose), most preferably as sole carbon sources. Suitable promoters in this context include promoters as described above for expression of the nucleotide sequences encoding xylose isomerases as defined above.

A further preferred cell of the invention comprises a genetic modification that reduces unspecific aldose reductase activity in the cell. Preferably, unspecific aldose reductase activity is reduced in the host cell by one or more genetic modifications that reduce the expression of or inactivates a gene encoding an unspecific aldose reductase. Preferably, the genetic modifications reduce or inactivate the expression of each endogenous copy of a gene encoding an unspecific aldose reductase that is capable of reducing an aldopentose, including, xylose, xylulose and arabinose, in the cell's genome. A given cell may comprise multiple copies of genes encoding unspecific aldose reductases as a result of di-, poly- or aneu-ploidy, and/or a cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell. A nucleotide sequence encoding an aldose reductase whose activity is to be reduced in the cell of the invention and amino acid sequences of such aldose reductases are described in WO 06/009434 and include e.g. the (unspecific) aldose reductase genes of *S. cerevisiae* GRE3 gene (Träff et al., 2001, Appl. Environm. Microbiol. 67: 5668-5674) and orthologues thereof in other species.

In a further preferred embodiment, the transformed cell of the invention that has the ability of isomerising xylose to xylulose as described above, in addition has the ability to convert L-arabinose into D-xylulose 5-phosphate as e.g. described in Wisselink et al. (2007, AEM Accepts, published online ahead of print on 1 Jun. 2007; Appl. Environ. Microbiol. doi:10.1128/AEM.00177-07) and in EP 1 499 708. The ability of to converting L-arabinose into D-xylulose 5-phosphate is preferably conferred to the cell by transformation with a nucleic acid construct(s) comprising nucleotide sequences encoding a) an arabinose isomerase; b) a ribulokinase, preferably a L-ribulokinase a xylose isomerase; and c) a ribulose-5-P-4-epimerase, preferably a L-ribulose-5-P-4-epimerase. Preferably, in the cells of the invention, the ability to convert L-arabinose into D-xylulose 5-phosphate is the ability to convert L-arabinose into D-xylulose 5-phosphate through the subsequent reactions of 1) isomerisation of arabinose into ribulose; 2) phosphorylation of ribulose to ribulose 5-phosphate; and, 3) epimerisation of ribulose 5-phosphate into D-xylulose 5-phosphate. Suitable nucleotide sequences encoding arabinose isomerases, a ribulokinases and ribulose-5-P-4-epimerases may be obtained from *Bacillus subtilis, Escherichia coli* (sec e.g. EP 1 499 708), Lactobacilli, e.g. *Lactobacillus plantarum* (see e.g. Wisselink et al. supra), or species of *Clavibacter, Arthrobacter* and *Gramella*, of which preferably *Clavibacter michiganensis, Arthrobacter aurescens* and *Gramella forsetii*.

A further preferred transformed host cell according to the invention may comprises further genetic modifications that result in one or more of the characteristics selected from the group consisting of (a) increased transport of xylose and/or arabinose into the cell; (b) decreased sensitivity to catabolite repression; (c) increased tolerance to ethanol, osmolarity or organic acids; and, (d) reduced production of by-products. By-products are understood to mean carbon-containing molecules other than the desired fermentation product and include e.g. xylitol, arabinitol, glycerol and/or acetic acid. Any genetic modification described herein may be introduced by classical mutagenesis and screening and/or selection for the desired mutant, or simply by screening and/or selection for the spontaneous mutants with the desired characteristics. Alternatively, the genetic modifications may consist of overexpression of endogenous genes and/or the inactivation of endogenous genes. Genes the overexpression of which is desired for increased transport of arabinose and/or xylose into the cell are preferably chosen form genes encoding a hexose or pentose transporter. In *S. cerevisiae* and other yeasts these genes include HXT1, HXT2, HXT4, HXT5, HXT7 and GAL2, of which HXT7, HXT5 and GAL2 are most preferred (see Sedlack and Ho, Yeast 2004; 21: 671-684). Another preferred transporter for expression in yeast is the glucose transporter encoded by the *P. stipitis* SUT1 gene (Katahira et al., 2008, Enzyme Microb. Technol. 43: 115-119). Similarly orthologues of these transporter genes in other species may be overexpressed. Other genes that may be overexpressed in the cells of the invention include genes coding for glycolytic enzymes and/or ethanologenic enzymes such as alcohol dehydrogenases. Preferred endogenous genes for inactivation include hexose kinase genes e.g. the *S. cerevisiae* HXK2 gene (see Diderich et al., 2001, Appl. Environ. Microbiol. 67: 1587-1593); the *S. cerevisiae* MIG1 or MIG2 genes; genes coding for enzymes involved in glycerol metabolism such as the *S. cerevisiae* glycerol-phosphate dehydrogenase 1 and/or 2 genes; or (hybridising) orthologues of these genes in other species. Other preferred further modifications of host cells for xylose fermentation are described in van Maris et al. (2006, Antonie van Leeuwenhoek 90:391-418), WO2006/009434, WO2005/023998, WO2005/111214, and WO2005/091733. Any of the genetic modifications of the cells of the invention as described herein are, in as far as possible, preferably introduced or modified by self cloning genetic modification.

In a preferred transformed host cell according to the invention, the nucleic acid construct confers to the host cell the ability to grow on xylose as carbon/energy source, preferably as sole carbon/energy source, and preferably under anaerobic conditions, i.e. conditions as defined herein below for anaerobic fermentation process. Preferably, when grown on xylose as carbon/energy source the transformed host produces essentially no xylitol, e.g. the xylitol produced is below the detection limit or e.g. less than 5, 2, 1, 0.5, or 0.3% of the carbon consumed on a molar basis. Preferably, in case carbon/energy source also includes arabinose, the cell produces essentially no arabinitol, e.g. the arabinitol produced is below the detection limit or e.g. less than 5, 2, 1, 0.5, or 0.3% of the carbon consumed on a molar basis.

A transformed host cell of the invention preferably has the ability to grow on xylose as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 h$^{-1}$ under anaerobic conditions. A cell of the invention preferably has the ability to grow on a mixture of glucose and xylose (in a 1:1 weight ratio) as sole carbon/energy source at a rate of at least 0.01, 0.02, 0.05, 0.1, 0.2, 0.25 or 0.3 h$^{-1}$ under aerobic conditions, or, more preferably, at a rate of at least 0.005, 0.01, 0.02, 0.05, 0.08, 0.1, 0.12, 0.15 or 0.2 h$^{-1}$ under anaerobic conditions. Thus, in a preferred transformed host cell according to the invention, the nucleic acid construct confers to the host cell the ability to anaerobically ferment xylose as sole carbon source in a process wherein ultimately pyruvate is used as an electron (and hydrogen acceptor) and is reduced to fermentation products such as ethanol, lactic acid, 3-hydroxy-propionic acid, acrylic acid, acetic acid, succinic acid, citric acid, amino acids, 1,3-propane-diol, ethylene, glycerol, β-lactam antibiotics and cephalosporins.

Preferably, a cell of the invention has a specific xylose consumption rate of at least 200, 300, 400, 600, 700, 800, 900 or 1000 mg h–1 (g dry weight)–1. Preferably, a cell of the invention has a yield of fermentation product (such as ethanol) on xylose that is at least 20, 40, 50, 60, 80, 90, 95 or 98% of the cell's yield of fermentation product (such as ethanol) on glucose. More preferably, the modified host cell's yield of fermentation product (such as ethanol) on xylose is equal to the host cell's yield of fermentation product (such as ethanol) on glucose. Likewise, the modified host cell's biomass yield on xylose is preferably at least 55, 60, 70, 80, 85, 90, 95 or 98% of the host cell's biomass yield on glucose. More preferably, the modified host cell's biomass yield on xylose is equal to the host cell's biomass yield on glucose. It is understood that in the comparison of yields on glucose and xylose both yields are compared under aerobic conditions or both under anaerobic conditions.

In another aspect the invention relates to a process for producing a fermentation product selected from the group consisting of ethanol, lactic acid, 3-hydroxy-propionic acid, acrylic acid, acetic acid, succinic acid, citric acid, amino acids, 1,3-propane-diol, ethylene, glycerol, β-lactam antibiotics and cephalosporins. The process preferably comprises the steps of: a) fermenting a medium containing a source of xylose, and optionally arabinose, with a cell as defined hereinabove, whereby the cell ferments xylose, and optionally arabinose, to the fermentation product, and optionally, b) recovery of the fermentation product.

In addition to a source of xylose the carbon source in the fermentation medium may also comprise a source of glucose. The skilled person will further appreciate that the fermentation medium may further also comprise other types of carbohydrates such as e.g. in particular a source of arabinose. The sources of xylose, glucose and arabinose may be xylose, glucose and arabinose as such (i.e. as monomeric sugars) or they may be in the form of any carbohydrate oligo- or polymer comprising xylose, glucose and/or arabinose units, such as e.g. lignocellulose, arabinans, xylans, cellulose, starch and the like. For release of xylose, glucose and/or arabinose units from such carbohydrates, appropriate carbohydrates (such as arabinases, xylanases, glucanases, amylases, cellulases, glucanases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases preferably during the fermentation. This, in turn, will prevent repression of systems required for metabolism and transport of non-glucose sugars such as xylose and arabinose. In a preferred process the modified host cell ferments both the xylose and glucose, and optionally arabinose, preferably simultaneously in which case preferably a modified host cell is used which is insensitive to glucose repression to prevent diauxic growth. In addition to a source of xylose (and glucose) as carbon source, the fermentation medium will further comprise the appropriate ingredient required for growth of the modified host cell. Compositions of fermentation media for growth of eukaryotic microorganisms such as yeasts and filamentous fungi are well known in the art.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$. Thus, in a preferred anaerobic fermentation process pyruvate is used as an electron (and hydrogen acceptor) and is reduced to fermentation products such as ethanol, as well as non-ethanol fermentation products such as lactic acid, 3-hydroxy-propionic acid, acrylic acid, acetic acid, succinic acid, citric acid, amino acids, 1,3-propane-diol, ethylene, glycerol, butyric acid, caproate, butanol, glyoxylate, β-lactam antibiotics and cephalosporins. Anaerobic processes of the invention are preferred over aerobic processes because anaerobic processes do not require investments and energy for aeration and in addition, anaerobic processes produce higher product yields than aerobic processes. Alternatively, the fermentation process of the invention may be run under aerobic oxygen-limited conditions. Preferably, in an aerobic process under oxygen-limited conditions, the rate of oxygen consumption is at least 5.5, more preferably at least 6 and even more preferably at least 7 mmol/L/h.

The fermentation process is preferably run at a temperature that is optimal for the modified cells of the invention. Thus, for most yeasts or fungal cells, the fermentation process is performed at a temperature which is less than 42° C., preferably less than 38° C. For yeast or filamentous fungal cells, the fermentation process is preferably performed at a temperature which is lower than 35, 33, 30 or 28° C. and at a temperature which is higher than 20, 22, or 25° C.

Preferably in the fermentation processes of the invention, the cells stably maintain the nucleic acid constructs that confer to the cell the ability of isomerising xylose into xylulose, and optionally converting arabinose into D-xylulose 5-phosphate. Preferably in the process at least 10, 20, 50 or 75% of the cells retain the abilities of isomerising xylose into xylulose, and optionally converting arabinose into D-xylulose 5-phosphate after 50 generations of growth, preferably under industrial fermentation conditions.

A preferred fermentation process according to the invention is a process for the production of ethanol, whereby the process comprises the steps of: a) fermenting a medium containing a source of xylose, and optionally arabinose, with a cell as defined hereinabove, whereby the cell ferments xylose, and optionally arabinose, to ethanol, and optionally, b) recovery of the ethanol. The fermentation medium may further be performed as described above. In the process the volumetric ethanol productivity is preferably at least 0.5, 1.0, 1.5, 2.0, 2.5, 3.0, 5.0 or 10.0 g ethanol per liter per hour. The ethanol yield on xylose and/or glucose and/or arabinose in the process preferably is at least 50, 60, 70, 80, 90, 95 or 98%. The ethanol yield is herein defined as a percentage of the theoretical maximum yield, which, for xylose, glucose and arabinose is 0.51 g. ethanol per g. xylose, glucose or arabinose.

A further preferred fermentation process according to the invention is a process which comprises fermenting a medium containing a source of xylose and a source of arabinose wherein however two separate strains of cells are used, a first strain of cells as defined hereinabove except that cells of the first strain do not have the ability to converting arabinose into D-xylulose 5-phosphate, which cells of the first strain ferment xylose to the fermentation product; and a second strain of cells as defined hereinabove except that cells of the second strain do not have the ability to (directly) isomerise xylose to xylulose, which cells of the second strain ferment arabinose to the fermentation product. The process optionally comprises the step of recovery of the fermentation product. The cells of the first and second are further as otherwise described hereinabove.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURE

FIG. 1 Phylogenetic tree of xylose isomerases tested for expression in yeast.

EXAMPLES

1. Functional Expression of Xylose Isomerases of the Invention in Yeast
1.1 Host Organism The yeast host strain was RN1000. This strain is a derivative of strain RWB 218 (Kuyper et al., FEMS Yeast Research 5, 2005, 399-409). The plasmid pAKX002 encoding the *Piromyces* XylA is lost in RN1000. The genotype of the host strain is: MatA, ura3-52, leu2-112, gre3::hphMX, loxP-Ptpi::TAL1, loxP-Ptpi::RKI1, pUGPtpi-TKL1, pUGPtpi-RPE1, {p415 Padh1XKS1Tcyc1-LEU2}.
1.2 Expression-Constructs with Synthetic XI Genes Synthetic codon-optimised (for *Saccharomyces cerevisiae*) XI genes were cloned into a derivative of pRS306 (Sikorski R. S., Hieter P., 1989, "A system of shuttle vectors and yeast host strains designed for efficient manipulation of DNA in *Saccharomyces cerevisiae*" Genetics 122:19-27) comprising the *Saccharomyces cerevisiae* TPI1 promoter (899 bp) and the CYC1 terminator (288 bp) sequences, using XbaI (at the 5'-end of the synthetic genes) and BamHI (at the 3'-end of the synthetic genes) restriction sites. The first three nucleotides in front of the ATG were modified into AAA in order to optimize expression. Table 1 provides a list of the XI sequences that were tested and the corresponding SEQ ID NO's depicting the synthetic sequences. Genes were synthesized by GenScript Corporation (see www.genscript.com) and delivered cloned in pUC57 (GenBank Y14837.1). The TPI promoter was obtained using yeast genomic DNA as template in a PCR with primers:
forward: AAACCGGTTTCTTCTTCAGATTCCCTC (SEQ ID NO:31);
reverse: TTAGATCTCTAGATTTATGTATGTGTTTTTTG-TAGT SEQ ID NO:32). The CYC1 terminator was obtained using yeast genomic DNA as template in a PCR with primers:
forward: AAGAATTCGGATCCCCTTTTCCTTTGTCGA (SEQ ID NO:33);
reverse: AACTCGAGCCTAGGAAGCCTTCGAGCGTC (SEQ ID NO:34).
1.3 Transformation of the Host Organism and Selection of Transformants RN1000 was transformed with plasmids using the 'Gietz method' (Gietz et al., 1992, Nucleic Acids Res. 1992 Mar. 25; 20(6):1425). Primary selection of transformants was done on mineral medium (YNB+2% glucose) via uracil complementation.
1.4 Enzyme Assays Xylose isomerase activity is assayed at 37° C. in a reaction mixture containing 50 mM phosphate buffer (pH 7.0), 10 mM xylose, 10 mM $MgCl_2$ and a suitable amount of cell-free extract. One unit of activity is defined as the amount of enzyme producing 1 nmol of xylulose per min under the assay conditions. Xylulose formed is determined by the method of Dische and Borenfreund (Dische and Borenfreund, 1951, J. Biol. Chem. 192: 583-587) or by HPLC using a Biorad HPX-87N Column operated at 80° C. and eluated at 0.6 ml/min using 0.01 M $Na_2HPO_4$ as the eluens. Xylose and xylulose are detected by a Refractive Index detector at an internal temperature of 60° C.

Specific activity is expressed as units per mg protein. Protein is determined with the Bio-Rad protein reagent (Bio-Rad Laboratories, Richmond, Calif., USA) with bovine γ-globulin as a standard.
1.5 Physiological Characterisation of the Transformed Cells Transformed cells were colony-purified on minimal medium with glucose as sole carbon source several times. Subsequently colony-purified transformed cells are grown in shake flasks in the presence of oxygen on synthetic medium with 2% (w/v) xylose as carbon/energy source. The results are shown in Table 2 where "+" indicates that cells showed significant growth. The sign "−" denotes that no significant growth occurred.

Strains growing at the expense of xylose were subsequently tested for their ability to grow anaerobically at the expense of xylose with a concomitant formation of ethanol. Strains transformed with the xylose isomerases of *Cyllamyces aberensis, Ciona intestinalis, Clostridium difficile, Bacteroides fragilis* and *Fusobacterium mortiferum* were able to grow anaerobically on xylose with growth rates, biomass and ethanol yields comparable to those of the prior art *Piromyces* enzyme, e.g. comparable to those of RWB218 as previously described by Kuyper et al. (2005, FEMS Yeast Res. 5: 925-934). However, cells transformed with the *C. difficile* XI showed the best performance in xylose fermentation in terms of growth rate.

Similarly the transformed cells of the invention are also capable of mixed substrate utilisation. When the transformed cells are grown in a mixture of glucose and xylose (20 g $l^{-1}$ each) both sugars are completely consumed but glucose was the preferred substrate. Xylose consumption commences only after approximately 80% of the glucose is consumed. The ethanol produced accounted for the consumption of the total of glucose and xylose in each instance of the strains transformed with the xylose isomerases of *Cyllamyces aberensis, Ciona intestinalis, Clostridium difficile, Bacteroides fragilis* and *Fusobacterium mortiferum*.

TABLE 1

| Name | length | CAI Initial genes | CAI optimized genes | nucleotide SEQ ID NO | Amino acid SEQ ID NO |
|---|---|---|---|---|---|
| Piromyces_sp_E2 | 1314 | 0.547 | 0.996 | 18 | 3 |
| Cyllamyces_aberensis | 1314 | 0.569 | 0.989 | 19 | 4 |
| Clostridium_difficile | 1338 | 0.107 | 0.987 | 16 | 1 |
| Bacteroides_fragilis | 1320 | 0.104 | 0.976 | 20 | 7 |
| Ciona_intestinalis | 1371 | 0.119 | 0.993 | 17 | 2 |
| Thermotoga_maritima | 1335 | 0.097 | 0.983 | 23 | 10 |
| Haemophilus_somnus | 1320 | 0.145 | 1.000 | 24 | 11 |
| Physcomitrella_patens | 1440 | 0.090 | 0.988 | 26 | 13 |
| Arabidopsis_thaliana | 1434 | 0.154 | 1.000 | 25 | 12 |
| Arthrobacter_aurescens | 1188 | 0.082 | 0.988 | 22 | 9 |
| Burkholderia_phytofirmans | 1323 | 0.065 | 0.982 | 21 | 8 |
| Orpinomyces_sp._Ukk1 | 1314 | 0.515 | Not tested | Not tested | 5 |
| Fusobacterium_mortiferum | 1311 | 0.106 | 0.989 | 38 | 35 |

TABLE 2

| XI source organism | Growth on 2% xylose in synthetic medium | % amino acid identity with *Piromyces* XI |
|---|---|---|
| Piromyces | + | 100 |
| Cyllamyces aberensis | + | 91 |
| Physcomitrella patens | − | 52 |
| Arabidopsis thaliana | − | 51 |
| Haemophilus somnus | − | 49 |
| Ciona intestinalis | + | 47 |
| Clostridium difficile | + | 54 |
| Thermotoga maritima | − | 51 |
| Bacteroides fragilis | + | 78 |
| Burkholderia phytofirmans | − | 50 |
| Arthrobacter aurescens | − | 17 |
| Fusobacterium_mortiferum | + | 51 |

TABLE 3

Pairwise amino acid identities between xylose isomerases from various organisms as indicated.

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1 Piromyces_sp_E2 | | | | | | | | | | | | | | |
| 2 Bacteroides_fragilis | 78, 71 | | | | | | | | | | | | | |
| 3 Cyllamyces_aberensis | 91, 30 | 77, 57 | | | | | | | | | | | | |
| 4 Clostridium_difficile | 54, 00 | 52, 61 | 53, 78 | | | | | | | | | | | |
| 5 Ciona_intestinalis | 47, 83 | 45, 10 | 45, 30 | 52, 36 | | | | | | | | | | |
| 6 Fusobacterium_mortiferum | 50, 92 | 50, 45 | 51, 15 | 71, 79 | 50, 46 | | | | | | | | | |
| 7 Orpinomyces_sp_ukk1 | 94, 51 | 78, 03 | 91, 07 | 55, 38 | 47, 14 | 50, 23 | | | | | | | | |
| 8 Clostridium_phytofermentans | 53, 55 | 53, 88 | 54, 92 | 62, 56 | 46, 80 | 64, 68 | 54, 23 | | | | | | | |
| 9 Bacteroides_uniformis | 81, 24 | 90, 41 | 80, 55 | 55, 03 | 47, 49 | 52, 75 | 80, 55 | 54, 79 | | | | | | |
| 10 Thermotoga_maritima | 51, 26 | 51, 02 | 51, 72 | 65, 99 | 50, 67 | 64, 91 | 50, 11 | 59, 82 | 52, 28 | | | | | |
| 11 Haemophilus_somnus | 48, 74 | 49, 43 | 49, 20 | 49, 89 | 45, 10 | 52, 06 | 48, 74 | 53, 42 | 50, 68 | 51, 03 | | | | |
| 12 Arabidopsis_thaliana | 51, 49 | 51, 71 | 52, 40 | 53, 03 | 51, 10 | 53, 90 | 51, 26 | 49, 77 | 52, 97 | 55, 41 | 48, 75 | | | |
| 13 Physcomitrella_patens | 51, 72 | 52, 39 | 52, 17 | 52, 81 | 51, 31 | 52, 75 | 51, 03 | 50, 68 | 53, 42 | 55, 86 | 48, 29 | 70, 23 | | |
| 14 Burkholderia_phytofirmans | 49, 43 | 48, 74 | 48, 74 | 48, 18 | 44, 77 | 49, 09 | 48, 98 | 50, 23 | 50, 23 | 49, 09 | 64, 69 | 46, 36 | 47, 05 | |
| 15 Arthrobacter_aurescens | 20, 76 | 20, 76 | 20, 76 | 19, 75 | 20, 51 | 20, 25 | 20, 76 | 21, 52 | 20, 25 | 20, 51 | 19, 49 | 19, 24 | 20, 25 | 20, 76 |

TABLE 4

| Organism | SEQ ID NO: | Multiple Sequence Alignment |
|---|---|---|

CLUSTAL W (1.83) multiple sequence alignment 1/5

```
Arabidopsis thaliana        12    MKKVEFFMLLLCFIAASSLVSADPPTCPADLGGKCSDSDDWQGDFFPEIPKIKYE-GPSS
Physcomitrella patens       13    MKALLFSVVLLVAVLSCSGQRVADITCGVDG-SLGSDFQEWEGEFFPNISYIKYE-GPAS
Ciona intestinalis           2    ----------------------MSSFAPASGKSDLAEAGSLLTKYPLEVKKIPYKPDAKV
Piromyces sp E2              3    ------------------------------------------MAKEYFPQIQKIKFE-GKDS
Orpinomyces sp ukk1          5    ------------------------------------------MTKEYFPTIGKIRFE-GKDS
Cyllamyces aberensis         4    ------------------------------------------MVKEYFPAIQKIKFE-GKDS
Bacteroides fragilis         7    ------------------------------------------MATKEYFPGIGKIKFE-GKDS
Bacteroides uniformis       37    ------------------------------------------MATKEYFPGIGKIKFE-GKES
Clostridium difficile        1    -------------------------------------------MNEIFKGIGQIKFE-GVKS
Fusobacterium mortiferum    35    --------------------------------------------MEFFKGIDKVKYE-GVKT
Thermotoga maritima         10    -------------------------------------------MAEFFPEIPKIQFE-GKES
Clostridium phytofermentans 36    -------------------------------------------MKNYFPNVPEVKYE-GPNS
Haemophilus somnus          11    -------------------------------------------MSNYFDKIAKVNYE-GANS
Burkholderia phytofirmans    8    -------------------------------------------MSYFEHIPEIRYE-GPQS
Arthrobacter aurescens       9    ------------------------------------------------------------
```

TABLE 4-continued

| Organism | SEQ ID NO: | Multiple Sequence Alignment |
|---|---|---|
| Arabidopsis thaliana | 12 | KNPLAYRWYNAEEEILGKKMKDWFRFSVAFWHTFRGIGGDPFGAATKYWPWEDGINSVSM |
| Physcomitrella patens | 13 | HNPLAYKYYNAEELIFGKKMKDWLRFSVAFWHTFRGDGGDPFGSPTKRWPWDDGSNSLTV |
| Ciona intestinalis | 2 | DDVLCFRHYNESEVVMGKPMSDWLRFSVCYWHTFRGTGADPFGFPTLVRPWDDGTDSIEN |
| Piromyces sp E2 | 3 | KNPLAFHYYDAEKEVMGKKMKDWLRFAMAWWHTLCAEGADQFGGGTKSFPWNEGTDAIEI |
| Orpinomyces sp ukk1 | 5 | KNPMAFHYYDAEKEVMGKKMKDWLRFAMAWWHTLCADGADQFGVGTKSFPWNEGTDPIAI |
| Cyllamyces aberensis | 4 | KNPMAFRYYDAEKEIMGKKMKDWLRFAMAWWHTLCAEGSDQFGPGTKTFPWNEGTDPIEK |
| Bacteroides fragilis | 7 | KNPMAFRYYDAEKMINGRSMKDWLKFAMAWWHTLCAEGGDQFGGGTKQFPWNGDPDPVQA |
| Bacteroides uniformis | 37 | KNPMAFRYYDADKVIMGKKMSEWLKFAMAWWHTLCAEGGDQFGGGTKKFPWNGEADKVQA |
| Clostridium difficile | 1 | NNELAFRYYNPEQVVGNKTMKEHLRFAMSYWHTLCGEGNDPFGVGTVERPWNNITDPIEI |
| Fusobacterium mortiferum | 35 | NNLLAFAHYNPEEVILGKKMKDHLKFAMSYWHILTGEGTDPFGNATMDREWN-EYTPMEK |
| Thermotoga maritima | 10 | TNPLAFRFYDPNEVIDGKPLKDHLKFSVAFWHTFVNEGRDPFGDPTAERPWNRFSDPMDK |
| Clostridium phytofermentans | 36 | TNPFAFKYYDANKVVAGKTMKEHCRFALSWWHTLCAGGADPFGVTTMDRTYGNITDPMEL |
| Haemophilus somnus | 11 | TNPFAFKHYNPNEVILGKTVEEHLRLAVCYWHTFCWTGNDMFGAGSLDRSWQKTGDLLVG |
| Burkholderia phytofirmans | 8 | DNPLAYRHYDKSKKVLGKTLEEHLRIAVCYWHTFVWPGVDIFGQGTFRRPWQQAGDAMER |
| Arthrobacter aurescens | 9 | ---------------MTPQPTPQDRFTFGLWTVG-WTGADPFGVATR------------- |
|  |  | ::: . * .    * * **    : |

CLUSTAL W (1.83) multiple sequence alignment 2/5

| Arabidopsis thaliana | 12 | AKRRMRANFEFLKKLGVDWWCFHDRDIAPDGTTLEESNKNLDEVIELAKELQKGSKIKPL |
| Physcomitrella patens | 13 | AVRRMRANFEFLKKLGVEKWCFHDRDIAPEGSTLEESNANLDYIVSVAKKLQEGTNIRPL |
| Ciona intestinalis | 2 | AERRMRVAFDFMSKLGVKYWTFHDRDIAPEGVTLSETNANLDRLAELASQLQGETGIKLL |
| Piromyces sp E2 | 3 | AKQKVDAGFEIMQKLGIPYYCFHDVDLVSEGNSIEEYESNLKAVVAYLKEKQKETGIKLL |
| Orpinomyces sp ukk1 | 5 | AKQKVDAGFEIMTKLGIEHYCFHDVDLVSEGNSIEEYESNLKQVVAYLKQKQQETGIKLL |
| Cyllamyces aberensis | 4 | AKQKVDAGFEIMTKLGIEHYCFHDVDLVDEGKNVEEYEKNLKTIVAYLKEKQKETGIKLL |
| Bacteroides fragilis | 7 | AKNKMDAGFEFMQKMGIGYYCFHDVDLVTEADSIEAYEANLKELVAYAKQKQAETGIKLL |
| Bacteroides uniformis | 37 | AKNKMDAGFEFMEYYCFHDVDLCEEAETIEEYEANLKEIVAYAKQKQAETGIKLL |
| Clostridium difficile | 1 | AKIKVDAGFEFMSKMGIEYFCFHDRDIAPEGRDLEETNKILDEIVEYIKANMEKTGIKLL |
| Fusobacterium mortiferum | 35 | AKARVKAGFEFMEKLGLEYFCFHDKDIAPEAETLEEYHRNLDEIVDLIEEEMKRTGIKLL |
| Thermotoga maritima | 10 | AFARVDALFEFCEKLNIEYFCFHDRDIAPEGKTLRETNKILDKVVERIKERMKDSNVKLL |
| Clostridium phytofermentans | 36 | AKAKVDAGFELMTKLGIEFFCFHDLDIAPEGDTFEESKKNLFEIVDYIKEKMDQTGIKLL |
| Haemophilus somnus | 11 | AKQKAEIAFEFFQKLGVPYYSFHDVDIAPESNNFKEYLHNENTIVDILEKKQSETGVKLL |
| Burkholderia phytofirmans | 8 | AQQKADSAFEFFSKLGTPYYTFHDTDVSPEGSNLKEYSENFLRITDYLARKQESTGIKLL |
| Arthrobacter aurescens | 9 | PALDPVEAVHKLSELGAYGITFHDNDLVPFDATASER----DLILKNFKAALAETGLKTP |
|  |  | . .. ::. *** *:            :         : :: |

| Arabidopsis thaliana | 12 | WGTAQLFLHPRYMHGGATSSEVGVYAYAAAQVKKAMEVTHYLGGENYVFWGGREGYQTLL |
| Physcomitrella patens | 13 | WGTAQLFKHPRYMHGAATSPDVRVYAYAAAQVKKAIEVTKLLGGENYVFWGGREGYQTLL |
| Ciona intestinalis | 2 | WNTCNLFAHPRYSNGAATNADAHVVAYAAAQVKKSLEIGKKLGAENFVFWGGREGYHTLL |
| Piromyces sp E2 | 3 | WSTANVFGHKRYMNGASTNPDFDVVARAIVQIKNAIDAGIELGAENYVFWGGREGYMSLL |
| Orpinomyces sp ukk1 | 5 | WSTANVEGNPRYMNGASTNPDFDVVARAIVQIKNAMDAGIELGAENYVFWGGREGYMSLL |
| Cyllamyces aberensis | 4 | WSTANVFGHKRYMNGASTNPDFDVVARAIVQIKNAMDAGIELGAENYVFWGGREGYMSLL |
| Bacteroides fragilis | 7 | WGTANVFSHARYMNGAATNPDFDVVARAAVQIKNAIDATIELGGTNYVFWGGREGYMSLL |
| Bacteroides uniformis | 37 | WGTANVFGHARYMNGAATNPDFDVVARAAQIKNAIDATIELGGSNYVFWGGREGYMSLL |
| Clostridium difficile | 1 | WGTANMEGNPREVHGASTTCNADVYAYAAAQVKKAMEITKYLGGENFVFWGGREGYETLL |
| Fusobacterium mortiferum | 35 | WGTSNMESHPREMHGAATSCNADVFAYAAAQTKKALEITKRLNGTGYVFWGGREGYETLL |
| Thermotoga maritima | 10 | WGTANLFSHPRYMHGAATTCSADVFAYAAAQVKKALEITKELGGEGYVFWGGREGYETLL |
| Clostridium phytofermentans | 36 | WGTANVFSPRFMHGASTSCNADVFAYAAAKIKNALDATIKLGGKGYVFWGGREGYETLL |
| Haemophilus somnus | 11 | WGTANCFTNPRYMSGASTNPNPEVFAWAAAQVFTAMNATQRLGGENYVLWGGREGYETLL |
| Burkholderia phytofirmans | 8 | WGTANLFSHPRYAAGAATSPDPEVFAFAATQVRHALDATQRLGGDNYVLWGGREGYDTLL |
| Arthrobacter aurescens | 9 | MVTTNLFSHPVFKDGGFTSNDRSIRRFALSKILRNIDLAAELGAETFVMWGGREGSEYDG |
|  |  | * : * : :  * . * .  . :   *   :   ::   *.. :*:****** |

CLUSTAL W (1.83) multiple sequence alignment 3/5

| Arabidopsis thaliana | 12 | NTDMGRGLDHLARFFEAAVAYKKKIGFKGILLIEPKPQEPTKHQYDWDAATAANFLRKY- |
| Physcomitrella patens | 13 | NTDLKKELDHMATFLRSAAEYKKKIGFEGTLLLEPKPQEPTKHQYDWDAATTMGFLKNYG |
| Ciona intestinalis | 2 | NTNVREELDNLANFFKMVVAYKKKIGFTGQFLIEPKPKEPSKHQYDYDAMTVIAFLKTY- |
| Piromyces sp E2 | 3 | NTDQKREKEHMATMLTMARDYARSKGFKGTELIEPKPMEPTKHQYDVDTETAIGFLKAHN |
| Orpinomyces sp ukk1 | 5 | NTDQKREKEHMATMLTMARDYARSKGFKGTELIEPKPMEPTKHQYDVDTETVIGFLRAHN |
| Cyllamyces aberensis | 4 | NTDQKREKEHMAMMLGLARDYARSKGFKGTELIEPKPMEPTKHQYDVDTETVIGFLRAHG |
| Bacteroides fragilis | 7 | NTDQKREKEHLAQMLTIARDYGRARGFKGTELIEPKPMEPTKHQYDVDTETVIGFLKAHG |
| Bacteroides uniformis | 37 | NTDQKREKEHLAQMLTIARDYARARGFKGTELIEPKPMEPTKHQYDVDTETVIGFLKAHN |
| Clostridium difficile | 1 | NTNTELEMDNFARFLQMAVDYAKEIGFTGQFLIEPKPKEPTKHQYDFDTATVLGFLRKYN |
| Fusobacterium mortiferum | 35 | NTDIGLELDNLARFLQMAVEYGGPFIEPKPKEPTKHQYDFDTTTVLEFLRKYN |
| Thermotoga maritima | 10 | NTDLGLELENLARFLRMAVEYAKKIGFTGQFLIEPKPKEPTKHQYDFDVATAYAFLKNHG |
| Clostridium phytofermentans | 36 | NTDLGLELDNMARLMKMAVEYGRANGEDGDFYIEPKPKEPTKHQYDFDTATVLAFLRKYG |
| Haemophilus somnus | 11 | NTDLKREREQIGRFMQLVVEHKYKIGFQGTLLIEPKPQEPTKHQYDYDVATVYGFLKQFG |
| Burkholderia phytofirmans | 8 | NTDLVRERDQLARFLHMVVDHAHKIGFKGSLLIEPKPNEPRGDIFLPTVGHGLAFIAQLE |
| Arthrobacter aurescens | 9 | SKDLSAALDRMKEGVDTAAGYIKEKGYGLRIALEPKPNEPRGDIFLPTVGHGLAFIAQLE |
|  |  | ..: ::: . . : *: : :**** ** . :     *: |

| Arabidopsis thaliana | 12 | --GLIDEFKLNIECNHATLSGHTCHHELETARINGLLGNIDANTGDAQTGWDTDQFLTDV |
| Physcomitrella patens | 13 | LSGTNNDYKLNLECNHATLSGHSCHHELETARIYGMLGSVDANTGDAQTGWDTDQFLTDV |
| Ciona intestinalis | 2 | -DLDKDFKLNIEPNHTTLAGHCEHDVVMASAYNMLGSVDSNTGSPDLGWDTDQFPMDV |
| Piromyces sp E2 | 3 | ---LDKDFKVNIEVNHATLAGHTFEHELACAVDAGMLGSIDANRGDYQNGWDTDQFPIDQ |
| Orpinomyces sp ukk1 | 5 | ---LDKDFKVNIEVNHATLAGHTFEHELACAVDAGMLGSIDANRGDYQNGWDTDQFPIDQ |
| Cyllamyces aberensis | 4 | ---LDKDFKINIEVNHATLAGHTFEHELACAVDAGMLGSIDANRGDYQNGWDTDQFPIDQ |

TABLE 4-continued

| Organism | SEQ ID NO: | Multiple Sequence Alignment |
|---|---|---|
| Bacteroides fragilis | 7 | ---LNQDFKVNIEVNHATLAGHTFEHELAVAVDNGMLGSIDANRGDYQNGWDTDQFPIDN |
| Bacteroides uniformis | 37 | ---LDKDFKVNIEVNHATLAGHTFEHELAVAVDNGMLGSIDANRGDYQNGWDTDQFPIDN |
| Clostridium difficile | 1 | ---LDKYFKVNIEANHATLAGHTFQHELNIARINNVLGSIDANQGDLLLGWDTDQFPTNI |
| Fusobacterium mortiferum | 35 | ---LDKYFKMNIEANHATLAGHTFQHELCTARINGVEGSIDANQGDMLLGWDTDQFPTNV |
| Thermotoga maritima | 10 | ---LDEYFKFNIEANHATLAGHTFQHELRMARILGKLGSIDANQGDLLLGWDTDQFPTNI |
| Clostridium phytofermentans | 36 | ---LEKDFKMNIEANHATLAGHTFEHELAMARVNGAFGSVDANQGDPNLGWDTDQFPTDV |
| Haemophilus somnus | 11 | ---LENEIKVNIEANHATLAGHTFQHEIATATSLGIFGSIDANRGDPQLGWDTDQFPNSV |
| Burkholderia phytofirmans | 8 | ---LDKEIRVNIEANHATLAGHSFHHEIATAYALGIFGSVDANRGDPQNGWDTDQFPNSV |
| Arthrobacter aurescens | 9 | HG---DIVGLNPETGHEQMAGLNFTHGIAQALWAGKLFHIDLN-GQRGIKYDQDLVFGHG |
| | | . .* . .* . ::* * : * . : :* * *. :* *. |

CLUSTAL W (1.83) multiple sequence alignment 4/5

| Organism | SEQ ID NO: | Multiple Sequence Alignment |
|---|---|---|
| Arabidopsis thaliana | 12 | GEATMVMMSVIKNGGIAPGGENFDAKLRRES--TDVEDLFIAHISGMDTMARGLRNAVKI |
| Physcomitrella patens | 13 | SEATLIMLSVIKNGGLAPGGENFDAKLRRES--VDVEDLFIAHISGMDTIARGLRNAAKL |
| Ciona intestinalis | 2 | KNATMIMQTVLEQGGLAPGGLNFDCKVRRES--TDVIDMMIAHVGAMDCFAKALKIAAKI |
| Piromyces sp E2 | 3 | YELVQAWMEIIRGGGFVTGGTNFDAKTRRNS--TDLEDIIIAHVSGMDAMARALENAAKL |
| Orpinomyces sp ukk1 | 5 | YELVQAWMEIIRGGGFVIGGTNFDAKTRRNS--TDLEDIIIAHISGMDAMARALENAAKL |
| Cyllamyces aberensis | 4 | YELVQAWMEIIRGGGFTTGGINFDAKTRRNS--TDLEDIIIAHISGMDAMARALENAAKL |
| Bacteroides fragilis | 7 | FELTQAMMQIIRNDGLGNGGINFDAKTRRNS--TDPEDIFIAHIAGMDAMARALESAANL |
| Bacteroides uniformis | 37 | FELTQAMMQIIRNGGFGNGGINFDAKTRRNS--TDLEDIFIAHIAGMDVMARALESAAKL |
| Clostridium difficile | 1 | YDATLAMYEVLKQGGIAPGGENFDSKVRRAS--FEVEDLFLAYIAGMDTFAKGLLIAHKL |
| Fusobacterium mortiferum | 35 | YDAVLAMYETLLAGGFKEGGLNFDAKVRRGS--FEPKDLFYAYISGMDTFAKGLKVAAKL |
| Thermotoga maritima | 10 | YDTTLAMYEVIKAGGFTKGGLNFDAKVRRAS--YKVEDLFIGHIAGMDTFALGFKIAYKL |
| Clostridium phytofermentans | 36 | HSATLAMLEVLKAGGFINGGLNEDAKVRRGS--FEFDDIAYGYIAGMDTFALGLIKAAEI |
| Haemophilus somnus | 11 | EENTLAMYEILKAGGFTTGGENFDAKIRRQS--TDPYDLFHAHIGAMDVLALSLKRAAKM |
| Burkholderia phytofirmans | 8 | EELTLAFYEILKHGGFTTGGMNFDSKVRRQS--VDPEDLFYGHIGAIDNLALAVERAAVL |
| Arthrobacter aurescens | 9 | DLTSAFFTVDLLENGFPNGGPKYDGPRHFDYKPSRTDGYDGVWESAKSNMSMYLLLKERA |
| | | : .*: ** ::* : . .. :: . |

| Organism | SEQ ID NO: | Multiple Sequence Alignment |
|---|---|---|
| Arabidopsis thaliana | 12 | LEEGSLSELVRKRYATWDSELGKQIEEGKADFEYLEKKAKEF-GEPKVSSAKQELAEMIF |
| Physcomitrella patens | 13 | LEEGRLTKLVEDRYSSENSPLGKTIEEGKVGFEELEKISLEA-EEPPITSGKQELAEMIF |
| Ciona intestinalis | 2 | REDGVLGKMKKERYASFGSGLGLKIKTGTATLEECDSFIQEN-GEPAKLSGKQEMFEAVL |
| Piromyces sp E2 | 3 | LQESPYTKMKKERYASFDSGIGKDFEDGKLTLEQVYEYGKKN-GEPKQTSGKQELYEAIV |
| Orpinomyces sp ukk1 | 5 | LQESPYCNMKKERYASEDSGIGKDFEDGKLTLEQVYEYGKKN-GEPKVISGKQELYEAIV |
| Cyllamyces aberensis | 4 | LTESPYKKMKKERYASFDSGMGKDFEDGKLTFEQVYEYGKKV-NEPKQTSGKQELYEAIV |
| Bacteroides fragilis | 7 | LNESPYQKMLSDRYASFDAGKGKEFEEGKLSLEELVAYAKAN-GEPKQTSGQQELYEALV |
| Bacteroides uniformis | 37 | LEESPYKKMLADRYASFDSGKGKEFEDGKLTLEDLVAYAKAN-GEPKQTSGKQELYEAIV |
| Clostridium difficile | 1 | LEDEVFENFTKERYASFSEGIGKDIVEGKVGFKELESYALQM-PVIKNKSGRQEMLEAIL |
| Fusobacterium mortiferum | 35 | IEDGTFEKIKVERYSSYTTGIGKQIVNGEVGFEELSKYALTN-GVKKNSSGRQEMLENIL |
| Thermotoga maritima | 10 | AKDGVEDKEIEEKYRSFKEGIGKEIVEGKTDFEKLEEYIIDK-EDIELPSGKQEYLESLL |
| Clostridium phytofermentans | 36 | IDDGRIAKFVDDRYASYKTGIGKAIVDGTTSLEELEQYVLTH-SEPVMQSGRQEVLETIV |
| Haemophilus somnus | 11 | IEDQTLQKVVDNRYAGWDQELGQKILNGKASLEDLAKIVETQGLAPKPVSGQQEYLENLV |
| Burkholderia phytofirmans | 8 | IENDRLDQFKRQRYSGWDAEFGRKISSGDYSLSALAEEAMARGLNPQHASGHQELMENIV |
| Arthrobacter aurescens | 9 | LAFRADPEVQEALATSGVFELGEPTLNAGETTADLLADASAFDTFNADQAAERSFAFVRL |
| | | :. * . . :..:. . |

CLUSTAL W (1.83) multiple sequence alignment 5/5

| Organism | SEQ ID NO: | Multiple Sequence Alignment |
|---|---|---|
| Arabidopsis thaliana | 12 | QSAM--------- |
| Physcomitrella patens | 13 | YSYV--------- |
| Ciona intestinalis | 2 | NRYF--------- |
| Piromyces sp E2 | 3 | AMYQ--------- |
| Orpinomyces sp ukk1 | 5 | AMYQ--------- |
| Cyllamyces aberensis | 4 | AMYM--------- |
| Bacteroides fragilis | 7 | NIYSL-------- |
| Bacteroides uniformis | 37 | NMYC--------- |
| Clostridium difficile | 1 | NRYIYEVDTISNK |
| Fusobacterium mortiferum | 35 | NRYIYE------- |
| Thermotoga maritima | 10 | NSYIVKTIAELR- |
| Clostridium phytofermentans | 36 | NNILFR------- |
| Haemophilus somnus | 11 | NSYLYR------- |
| Burkholderia phytofirmans | 8 | NQAIYSGR----- |
| Arthrobacter aurescens | 9 | NQLAIEHLLGAR- |

The invention claimed is:

1. A yeast cell comprising a nucleic acid construct comprising a heterologous nucleic acid with a nucleotide sequence encoding a polypeptide that has xylose isomerase activity, the expression of which confers on, or increases in, the yeast cell the ability to directly isomerize xylose into xylulose, wherein the amino acid sequence of the polypeptide is at least 93% identical to SEQ ID NO:1 and comprises one or more conservative amino acid substitutions; wherein the one or more conservative amino acid substitutions is selected from the group consisting of valine to leucine or isoleucine, phenylalanine to tyrosine, lysine to arginine, and asparagine to glutamine.

2. The yeast cell according to claim 1, wherein the amino acid sequence of the polypeptide is at least 95% identical to SEQ ID NO: 1.

3. The yeast cell according to claim 1, wherein the heterologous nucleic acid is obtained from a bacterium of the genus *Clostridium*.

4. The yeast cell according to claim 1, wherein said yeast cell is a member of one of the following genera: *Saccharomyces, Kluyveromyces, Candida, Pichia, Schizosaccharomyces, Hansenula, Kloeckera, Schwanniomyces*, and *Yarrowia*.

5. The yeast cell according to claim 4, wherein the yeast cell is capable of anaerobic alcoholic fermentation.

6. The yeast cell according to claim 5, wherein the yeast cell is a member of one of the following species: *S. cerevisiae, S. exiguus, S. bayanus, K. lactis, K. marxianus* and *Schizosaccharomyces pombe*.

7. The yeast cell according to claim 1, wherein the heterologous nucleic acid is operably linked to a promoter that drives sufficient expression of the heterologous nucleic acid in the yeast cell to confer on the yeast cell the ability to isomerize xylose to xylulose.

8. The yeast cell according to claim 1, wherein said yeast cell further comprises a genetic modification that increases specific xylulose kinase activity by overexpression of a nucleic acid encoding a xylulose kinase, wherein the overexpression is by increasing the copy number of the nucleic acid or by placing the nucleic acid under the control of a heterologous promoter.

9. The yeast cell according to claim 1, wherein said yeast cell comprises a genetic modification that increases pentose phosphate pathway flux by overexpression of a nucleic acid encoding at least one enzyme selected from the group consisting of ribulose-5-phosphate isomerase, ribulose-5-phosphate 3-epimerase, transketolase and transaldolase, wherein the overexpression is by increasing the copy number of the nucleic acid or by placing the nucleic acid under the control of a heterologous promoter.

10. The yeast cell according to claim 1, wherein said yeast cell comprises a genetic modification that reduces the yeast cell's nonspecific aldose reductase activity by disruption of at least one endogenous copy of a gene encoding a nonspecific aldose reductase.

11. The yeast cell according to claim 1, wherein said yeast cell converts L-arabinose into D-xylulose 5-phosphate.

12. The yeast cell according to claim 1, wherein said yeast cell has the ability to produce at least one of the following fermentation products: ethanol, lactic acid, 3-hydroxy-propionic acid, acrylic acid, acetic acid, succinic acid, citric acid, an amino acid, 1,3-propane-diol, ethylene, glycerol, butyric acid, caproate, butanol, glyoxylate, a β-lactam antibiotic or a cephalosporin.

13. The yeast cell according to claim 1, wherein the heterologous nucleic acid is obtained from bacteria of the family Clostridiaceae.

14. The yeast cell according to claim 13, wherein said yeast cell is a member of one of the following genera: *Saccharomyces, Kluyveromyces, Candida, Pichia, Schizosaccharomyces, Hansenula, Kloeckera, Schwanniomyces*, and *Yarrowia*.

15. The yeast cell according to claim 14, wherein said yeast cell is capable of anaerobic alcoholic fermentation and is a member of one the following species: *S. cerevisiae, S. exiguus, S. bayanus, K. lactis, K. marxianus* and *Schizosaccharomyces pombe*.

16. The yeast cell according to claim 1, wherein said yeast cell
  (a) further comprises a genetic modification that
    (i) increases specific xylulose kinase activity by overexpression of a nucleic acid encoding a xylulose kinase;

(ii) increases pentose phosphate pathway flux by overexpression of a nucleic acid encoding at least one enzyme selected from the group consisting of ribulose-5-phosphate isomerase, ribulose-5-phosphate 3-epimerase, transketolase and transaldolase; or (iii) reduces the cell's nonspecific aldose reductase activity by disruption of at least one endogenous copy of a gene encoding a nonspecific aldose reductase;

wherein the overexpression is by increasing the copy number of the nucleic acid or by placing the nucleic acid under the control of a heterologous promoter; or (b) converts L-arabinose into D-xylulose 5-phosphate.

17. The yeast cell according to claim 13, wherein said yeast cell has the ability to produce at least one of the following fermentation products: ethanol, lactic acid, 3-hydroxy-propionic acid, acrylic acid, acetic acid, succinic acid, citric acid, an amino acid, 1,3-propane-diol, ethylene, glycerol, butyric acid, caproate, butanol, glyoxylate, a β-lactam antibiotic and a cephalosporin.

18. The yeast cell of claim 1, wherein the amino acid sequence of the polypeptide is at least 97% identical to SEQ ID NO:1.

19. A eukaryotic cell comprising:

(a) a heterologous nucleic acid encoding the polypeptide of SEQ ID NO: 1; or (b) a heterologous nucleic acid encoding a polypeptide having xylose isomerase activity, wherein said polypeptide comprises all of SEQ ID NO: 1 except for one amino acid substitution selected from the group consisting of valine to leucine or isoleucine, phenylalanine to tyrosine, lysine to arginine, alanine to valine, and asparagine to glutamine.

20. A process for producing a fermentation product comprising the steps of:

(a) culturing the yeast cell of claim 1 with a medium containing a source of xylose, and optionally a source of arabinose, to ferment xylose and obtain a fermentation product selected from the group consisting of ethanol, lactic acid, a 3-hydroxy-propionic acid, acrylic acid, acetic acid, succinic acid, citric acid, an amino acid, 1,3-propane-diol, ethylene, glycerol, butyric acid, caproate, butanol, glyoxylate, a β-lactam, an antibiotic and a cephalosporin, and, optionally, (b) recovering the fermentation production from the medium.

21. The process according to claim 20, wherein the medium also contains a source of glucose.

22. A process for producing a fermentation product comprising the steps of:

(a) culturing the yeast cell of claim 13 with a medium containing a source of xylose, and optionally a source of arabinose, to ferment xylose and obtain a fermentation product selected from the group consisting of ethanol, lactic acid, 3-hydroxy-propionic acid, acrylic acid, acetic acid, succinic acid, citric acid, an amino acid, 1,3-propane-diol, ethylene, glycerol, butyric acid, caproate, butanol, glyoxylate, a β-lactam, an antibiotic and a cephalosporin, and, optionally, (b) recovering the fermentation product from the medium.

23. A process for producing a fermentation product comprising the steps of:

(a) culturing the yeast cell of claim 3 with a medium containing a source of xylose, and optionally a source of arabinose, to ferment xylose and obtain a fermentation product selected from the group consisting of ethanol, lactic acid, 3-hydroxy-propionic acid, acrylic acid, acetic acid, succinic acid, citric acid, an amino acid, 1,3-propane-diol, ethylene, glycerol, butyric acid, caproate, butanol, glyoxylate, a β-lactam, an antibiotic and a cephalosporin, and, optionally, (b) recovering the fermentation product from the medium.

* * * * *